(12) United States Patent
Hedrick et al.

(10) Patent No.: US 10,995,177 B2
(45) Date of Patent: *May 4, 2021

(54) ANTIMICROBIAL POLYCARBONATES FOR MULTIDRUG RESISTANT BACTERIA

(71) Applicants: International Business Machines Corporation, Armonk, NY (US); Agency for Science, Technology and Research, Singapore (SG)

(72) Inventors: James L. Hedrick, Pleasanton, CA (US); Yi Yan Yang, Singapore (SG); Chuan Yang, Singapore (SG)

(73) Assignees: AGENCY FOR SCIENCE, TECHNOLOGY AND RESEARCH, Singapore (SG); CORAL BAY II, LLC., New York, NY (US)

( * ) Notice: Subject to any disclaimer, the term of this patent is extended or adjusted under 35 U.S.C. 154(b) by 212 days.

This patent is subject to a terminal disclaimer.

(21) Appl. No.: 16/013,474

(22) Filed: Jun. 20, 2018

(65) Prior Publication Data

US 2019/0390005 A1     Dec. 26, 2019

(51) Int. Cl.
```
C08G 64/02    (2006.01)
C08G 63/42    (2006.01)
A61P 31/04    (2006.01)
C08G 64/42    (2006.01)
B82Y 40/00    (2011.01)
B82Y 5/00     (2011.01)
```

(52) U.S. Cl.
CPC .......... *C08G 64/0241* (2013.01); *A61P 31/04* (2018.01); *C08G 64/42* (2013.01); *B82Y 5/00* (2013.01); *B82Y 40/00* (2013.01)

(58) Field of Classification Search
CPC ........... A61P 31/04; B82Y 40/00; B82Y 5/00; C08G 64/0241; C08G 64/42; C08G 64/30
See application file for complete search history.

(56) References Cited

U.S. PATENT DOCUMENTS

| | | | |
|---|---|---|---|
| 9,854,806 B2 * | 1/2018 | Chin | A61P 31/00 |
| 2007/0048345 A1 | 3/2007 | Huang et al. | |
| 2012/0301528 A1 | 11/2012 | Uhlmann et al. | |
| 2014/0301967 A1 | 10/2014 | Chin et al. | |
| 2015/0264932 A1 | 9/2015 | Coady et al. | |
| 2016/0338356 A1 * | 11/2016 | Chin | C08G 18/73 |
| 2017/0073471 A1 | 3/2017 | Breyta et al. | |
| 2017/0150714 A1 | 6/2017 | Schwarz | |
| 2017/0303541 A1 | 10/2017 | Chin et al. | |
| 2019/0388460 A1 * | 12/2019 | Hedrick | C08G 64/0241 |
| 2019/0390005 A1 | 12/2019 | Hedrick et al. | |

OTHER PUBLICATIONS

Yang ("Broad-Spectrum Antimicrobial Star Polycarbonates Functionalized with Mannose for Targeting Bacteria Residing inside Immune Cells", Advanced Healthcare Materials, vol. 5, Issue 11, Jun. 8, 2016, pp. 1272-1281). (Year: 2016).*

Chin, et al., "A macromolecular approach to eradicate multidrug resistant bacterial infections while mitigating drug resistance onset," Nature Communications | (2018) 9:917, DOI: 10.1038/s41467-018-03325-6, 14 pages.

Cho, et al., "Molecular Weight and Charge Density Effects of Guanidinylated Biodegradable Polycarbonates on Antimicrobial Activity and Selectivity," Received: Aug. 30, 2017, DOI: 10.1021/acs.biomac.7b01245, 13 pages.

Engler, et al., "Antimicrobial Polycarbonates: Investigating the Impact of Balancing Charge and Hydrophobicity Using a Same-Centered Polymer Approach," Biomacromolecules, 2013, 14 (12), 2 pages.

Nimmagadda, et al., "Polycarbonates with Potent and Selective Antimicrobial Activity toward Gram-Positive Bacteria," Biomacromolecules, Jan. 9, 2017; 18(1): 87-95. doi:10.1021/acs.biomac.6b01385, 24 pages.

Tejero, et al., "Tailoring Macromolecular Structure of Cationic Polymers towards Efficient Contact Active Antimicrobial Surfaces," Polymers 2018, 10, 241; doi:10.3390/polym10030241, 11 pages.

Liu, et al., "Highly potent antimicrobial polyionenes with rapid killing kinetics, skin biocompatibility and in vivo bactericidal activity," Biomaterials 127 (2017) pp. 36-48.

Pratt, et al., "Exploration, Optimization, and Application of Supramolecular Thiourea-Amine Catalysts for the Synthesis of Lactide (Co)polymers," Macromolecules 2006, 39, pp. 7863-7871.

Cooley, et al., "Oligocarbonate Molecular Transporters: Oligomerization-Based Syntheses and Cell-Penetrating Studies," J. Am. Chem. Soc. 2009, 131, pp. 16401-16403.

Pratt, et al., "Tagging alcohols with cyclic carbonate: a versatile equivalent of (meth)acrylate for ring-opening polymerization," The Royal Society of Chemistry 2007, 5 pages.

Xue, et al., "Antimicrobial Polymeric Materials with Quaternary Ammonium and Phosphonium Salts," Int. J. Mol. Sci. 2015, 16, pp. 3626-3655; doi:10.3390/ijms16023626.

(Continued)

*Primary Examiner* — Anna R Falkowitz
(74) *Attorney, Agent, or Firm* — Amin, Turocy & Watson, LLP

(57) ABSTRACT

Compositions and methods regarding guanidinium functionalized polycarbonates that provide potent antimicrobial activity against multidrug resistant (MDR) bacteria, including *Klebsiella pneumoniae* (*K. pneumoniae*) are provided. According to an embodiment, an antimicrobial guanidinium-functionalized polymer is provided that comprises a hydrophobic molecular backbone with cationic guanidinium moieties respectively bound to the hydrophobic molecular backbone via butyl spacer groups. The antimicrobial guanidinium-functionalized polymer self-assembles into a micelle structure with hydrophobic residuals of the antimicrobial guanidinium-functionalized polymer buried inside the micelle structure and the cationic guanidinium moieties exposed on an external surface of the micelle structure to target pathogens.

19 Claims, 17 Drawing Sheets

(56) References Cited

OTHER PUBLICATIONS

Yang, et al., "Broad-Spectrum Antimicrobial Star Polycarbonates Functionalized with Mannose for Targeting Bacteria Residing inside Immune Cells," Advanced Healthcare Materials, vol. 5, Issue 11 Jun. 8, 2016, 2 pages, https://onlinelibrary.wiley.com/doi/abs/10.1002/adhm.201600070.
Non-Final Office Action received for U.S. Appl. No. 16/013,499 dated May 15, 2020, 42 pages.
Final Office Action received for U.S. Appl. No. 16/013,499 dated Nov. 30, 2020, 44 pages.
Pranantyo et. al, "Increasing bacterial affinity and cytocompatibility with four-arm star glycopolymers and antimicrobial a-polylysine", Polymer Chemistry, 8, pp. 3364-3373, 2017 (Year: 2017).

* cited by examiner

Example Polymer Synthesis

MIC Values of Antimicrobial Agents Against Clinically Isolated MDR bacteria: K pneumoniae (K.P.), A.baumannii (A.B), P. aeruginosa (P.A.), E.coli, E. faecium (E.F.), and methicillin-resistant S. Aureus (MRSA)

| Agents | MIC (mg/L) | | | | | | | | | | | | |
|---|---|---|---|---|---|---|---|---|---|---|---|---|---|
| | K.P. 9170 | K.P. 9859 | A.B. 4123 | A. B. 10361 | P.A. 26121 | P.A. 25900 | E. Coli 56809 | E. Coli 58628 | E.F. 25300 | E.F. 25309 | MRSA 25312 | MRSA 25332 | MRSA 25343 |
| Structure IV | 64 | 64 | 16 | 16 | 32 | 32 | 16 | 32 | 32 | 32 | 8 | 16 | 16 |
| Structure V | 16 | 32 | 16 | 16 | 16 | 16 | 8 | 8 | 32 | 32 | 4 | 8 | 8 |
| Structure I | 8 | 16 | 16 | 16 | 16 | 16 | 8 | 8 | 16 | 16 | 4 | 4 | 8 |
| Imipenem | 64 | 64 | 32 | 32 | 64 | 16 | 0.25 | 0.25 | | | | | |
| Vancomycin | | | | | | | | | 0.5 | 64 | 2 | 2 | 2 |

FIG. 4

Cumulative Distribution of MIC Values Against K. pneumoniae (n = 25)

| Agents | Cumulative % of 25 K. pneumoniae strains at indicated MICs (mg/L) | | | | | | | | | |
|---|---|---|---|---|---|---|---|---|---|---|
| | 1 | 2 | 4 | 8 | 16 | 32 | 64 | 128 | 256 | 512 |
| Structure IV | | | | | 4 | 4 | 64 | 88 | 96 | 100 |
| Structure V | | | | 4 | 44 | 76 | 96 | 96 | 100 | |
| Structure I | | | | 16 | 60 | 80 | 100 | | | |
| Ceftiaxone | | | | | | | | 24 | 88 | 100 |
| Gentamycin | | | | | | 16 | 36 | 56 | 72 | 100 |
| Imipenem | | | | | 4 | 32 | 76 | 84 | 100 | |

FIG. 5

Efficacy of Antimicrobial Agents Against *K. pneumoniae* 9170 in an Immunosuppressed Pneumonia Mouse Model

| Strain | Minimal lethal dose (CFU/mouse) | Antimicrobial agent | LD50/LD5 (mg/kg) | ED50/ED95 (mg/kg) | Therapeutic index |
|---|---|---|---|---|---|
| KP 9170 | $1.25 \times 10^8$ | Structure IV | 44.2/43.1 | 3.79/15.1 | 11.6 |
| | | Structure V | 74.6/63.5 | 2.97/10.9 | 25.1 |
| | | Structure I | 158.0/141.8 | 1.78/8.38 | 88.8 |
| | | Imipenem | ND | 5.93/21.9 | ND |

FIG. 9

```
                    ┌──────────────────────────────────────┐
                    │ CONTACTING A BACTERIA MICROBE WITH AN │
                    │ ANTIMICROBIAL POLYMER HAVING A MICELLE│
                    │ STRUCTURE IN AN AQUEOUS SOLUTION,     │──1402
                    │ WHEREIN THE MICELLE STRUCTURE LOCATES │
                    │ HYDROPHOBIC RESIDUALS OF THE          │
                    │ ANTIMICROBIAL POLYMER INSIDE THE      │
                    │ MICELLE STRUCTURE AND CATIONIC        │
                    │ GUANIDINIUM MOIETIES EXPOSED ON AN    │
                    │ EXTERNAL SURFACE OF THE MICELLE       │
                    │ STRUCTURE                             │
                    └──────────────────────────────────────┘
                                      │
                                      ▼
                    ┌──────────────────────────────────────┐
                    │ BASED ON THE CONTACTING, FACILITATING │
                    │ CHARGE NATURALIZATION OF THE BACTERIAL│──1404
                    │ MEMBRANE VIA A COUNTERION EXCHANGE    │
                    │ BETWEEN THE CATIONIC GUANIDINIUM      │
                    │ MOIETIES AND NEGATIVELY CHARGED       │
                    │ PHOSPHATE GROUPS ON THE BACTERIAL     │
                    │ MEMBRANE                              │
                    └──────────────────────────────────────┘
                                      │
                                      ▼
                    ┌──────────────────────────────────────┐
                    │ FACILITATING TRANSLOCATION OF THE     │──1406
                    │ ANTIMICROBIAL POLYMER THROUGH THE     │
                    │ BACTERIAL MEMBRANE BASED ON THE       │
                    │ CHARGE NEUTRALIZATION                 │
                    └──────────────────────────────────────┘
```

FIG. 14

ANTIMICROBIAL POLYCARBONATES FOR MULTIDRUG RESISTANT BACTERIA

TECHNICAL FIELD

The subject disclosure relates antimicrobial polycarbonates and more particularly to one more guanidinium functionalized polycarbonates that provide potent antimicrobial activity against multidrug resistant (MDR) bacteria, including *Klebsiella pneumoniae* (*K. pneumoniae*).

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding guanidinium functionalized polycarbonates that provide potent antimicrobial activity against multidrug resistant (MDR) bacteria, including *Klebsiella pneumoniae* (*K. pneumoniae*).

According to an embodiment, an antimicrobial guanidinium-functionalized polymer is provided that comprises a hydrophobic molecular backbone with cationic guanidinium moieties respectively bound to the hydrophobic molecular backbone via butyl spacer groups. The antimicrobial guanidinium-functionalized polymer self-assembles into a micelle structure with hydrophobic residuals of the antimicrobial guanidinium-functionalized polymer buried inside the micelle structure and the cationic guanidinium moieties exposed on an external surface of the micelle structure to target pathogens. In one or more embodiments, the hydrophobic molecular backbone comprises polycarbonate. The micelle structure can be a nanostructure having a size between 20 and 300 nanometers (nm).

In various implementations, the hydrophobic residuals of the antimicrobial polymer interact with lipid domains of the cell membranes, which causes non-specific toxicity towards mammalian cells. In this regard, the micelle structure mitigates exposure of the hydrophobic residuals to mammalian cells in vivo. At the same time, the antimicrobial guanidinium-functionalized polymer is effective at killing Gram-negative bacteria and Gram-positive bacteria. In particular, the antimicrobial guanidinium-functionalized polymer is particularly effective at killing MDR strains of *K. pneumonia*. In some embodiments, the antimicrobial guanidinium-functionalized polymer is also effective at killing bacteria selected from a group consisting of: *Acinetobacter baumannii, Escherichia coli, Staphylococcus aureus,* methicillin-resistant *Staphylococcus aureus, Pseudomonas aeruginosa* and *Enterococcus faecium* (collectively known as the ESKAPE pathogens). The antimicrobial guanidinium-functionalized polymer is further biodegradable and biocompatible.

DESCRIPTION OF THE DRAWINGS

FIG. 4 presents an example, non-limiting table comparing the minimum inhibitory concentration (MIC) values of various antimicrobials, including the subject antimicrobial guanidinium polymers, against different strains of clinically isolated bacterial, in accordance with one or more embodiments described herein.

FIG. 5 presents an example, non-limiting table providing the cumulative MIC values of various antimicrobials, including the subject antimicrobial guanidinium polymers, against clinically isolated, MDR *K. pneumoniae* in accordance with one or more embodiments described herein.

FIG. 9 presents an example, non-limiting graph demonstrating the efficacy of various antimicrobials, including the subject antimicrobial guanidinium polymers, against *K. pneumoniae* in a *K. pneumoniae*-caused lung infection mouse model, in accordance with one or more embodiments described herein.

FIG. 14 illustrates a high-level flow diagram of an example, non-limiting method that can facilitate killing of a pathogen with one or more guanidinium macromolecules in accordance with one or more embodiments described herein.

DETAILED DESCRIPTION

Figure 1:
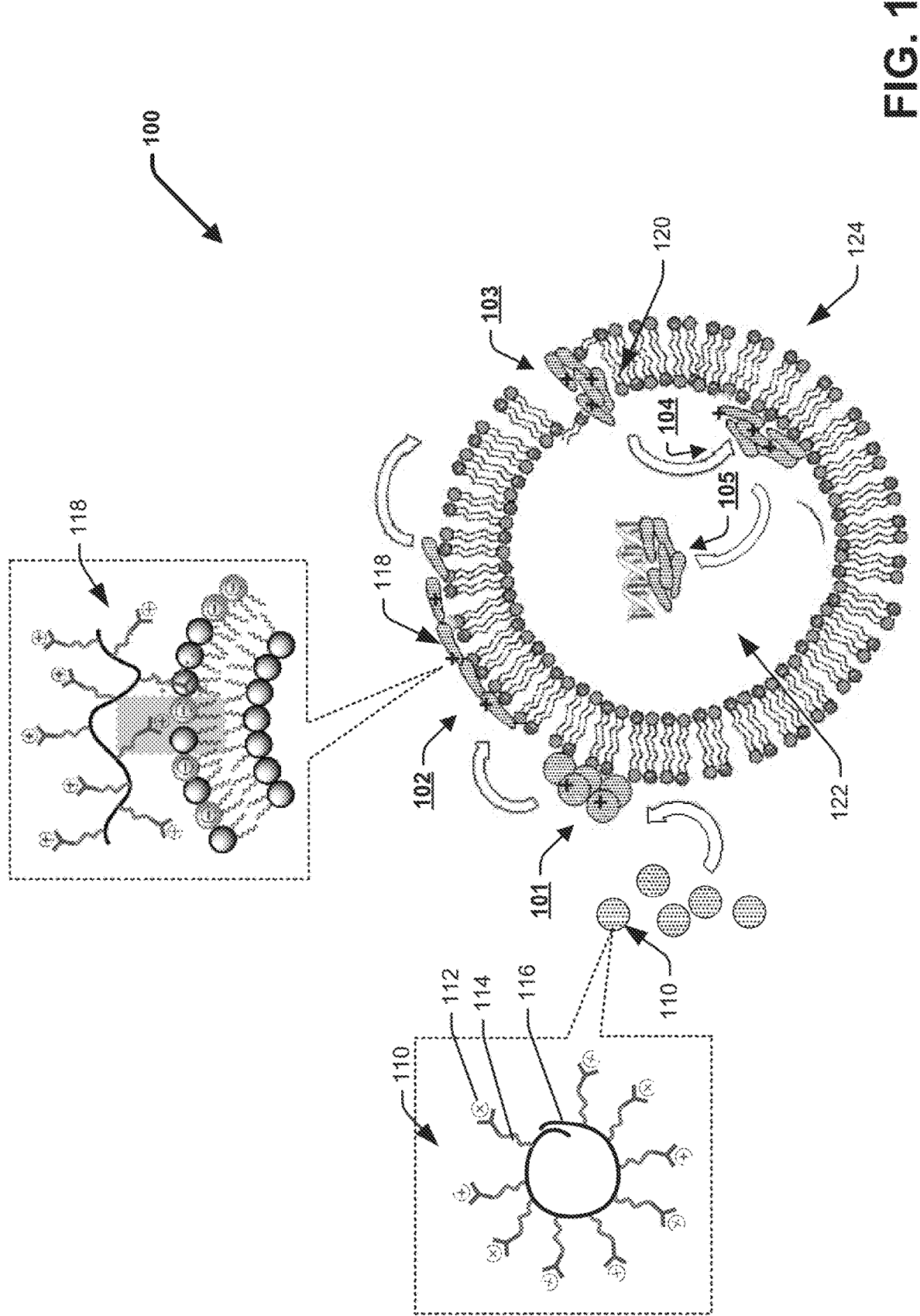
FIG. 1 provides a diagram illustrating an example, non-limiting, effective antimicrobial mechanism afforded one or more antimicrobial guanidinium functionalized polymers in accordance with one or more embodiments described herein.

The following detailed description is merely illustrative and is not intended to limit embodiments and/or application or uses of embodiments. Furthermore, there is no intention to be bound by any expressed or implied information presented in the preceding Summary and Description of the Drawings sections, or in the Detailed Description section.

The Gram-negative opportunistic bacterial pathogen *Klebsiella pneumoniae* (*K. pneumoniae*) found in the normal flora of the mouth, skin and intestine is responsible for a significant number of hospital-acquired infections. *K. pneumoniae*-induced *pneumoniae* is one of the most urgent global health threats owing to its severity, high incidence of complications, and a dreadful mortality rate which is up to approximately 50%, even with current antibiotic regimens. *K. pneumoniae* infections typically occur in patients compromised with asthma, allergic airway inflammation, cystic fibrosis, or chronic obstructive pulmonary, complicating the treatment regimen. Moreover, *K. pneumoniae* infections are the most commonly observed infections in livestock, leading to an over use of antibiotics is agriculture that leads to cross-resistance with these therapeutics. Over the last few years in clinical settings, a growing incidence of multidrug resistant (MDR) *K. pneumoniae* has been reported, limiting treatment options.

Carbapenems like imipenem and meropenem are considered the first line of defense for treating infections caused by MDR *K. pneumoniae*. However, the effectiveness of carbapenem derivatives for *K. pneumoniae* and related infections has produced a sharp increase of extended-spectrum beta-lactamase (ESBL)-producing *K. pneumoniae*, resulting in the emergence of carbapenem-resistant *K. pneumoniae* (CRKP). Although polymixins are widely recognized as the last line of defense against Gram-negative pathogens including CRKP, side effects often include grievous nephrotoxicity and neurotoxicity, limiting clinical applications. The emergence of polymyxin resistance has been attributed to chromosomal mutations that alter lipopolysaccharide composition, polysaccharide capsule formation or efflux pump function. Given the severity of *K. pneumoniae*-induced infections and the diminishing effectiveness of existing antibiotics against CRKP, it is exceedingly urgent to develop novel medication candidates against MDR *K. pneumonia*, while mitigating the onset of MDR.

The disclosed subject matter is directed to the development and application of one or more novel guanidinium-based antimicrobial polymers that selectively target and eradicate *K. pneumoniae* and other MDR bacteria, in vitro and in vivo, while minimizing toxicity and medication resistance onset. In some implementations, the disclosed guanidinium macromolecules can also be effective at killing fungi, yeast, and other pathogens. In one or more embodiments, the subject antimicrobial guanidinium-based polymers can comprise a hydrophobic polymer backbone consisting of one or more covalently bonded polymer units, wherein at least some (one or more) of the polymer units comprise a cationic (positively charged) guanidine-based functional group extending therefrom and covalently bonded to one or more atoms of the polymer unit via a butyl spacer group. In this regard, the polymer backbone can comprise one or more repeat monomer units that are respectively functionalized with a cationic, guanidine-based antimicrobial moiety. These monomers are referred to herein as guanidinium functionalized monomers.

In various embodiments, the subject guanidinium functionalized polymers can facilitate killing bacterial cells via membrane translocation followed by interacting with cytosolic materials (proteins and genes) and precipitating them inside the cells. In this regard, the polymer backbone and the one or more butyl spacer groups that connect the cationic guanidinium moieties thereto are hydrophobic (or substantially hydrophobic) in nature, while the cationic guanidinium moieties are hydrophilic in nature. When used as an antimicrobial, the cationic guanidinium moieties bind with the anionic (negatively charged) phosphate groups on the bacterial membrane surface, resulting in counterion exchange and charge neutralization that allows the polymer to translocate through the lipid bilayer of the bacterial membrane (e.g., as a non-polar species). The polymer is then released through the membrane leading to cytosol material precipitation and subsequent cell apoptosis. In this regard, the hydrophobic residuals and the guanidinium groups of the polymer are highly toxic to the bacterial biomolecules within the cytosol, and thus cause local disorder and precipitation within the cytosol, leading to cell apoptosis. The more hydrophobic the polymers, the more toxic they are to bacteria once internalized by the bacteria. However, the hydrophobic residuals of the polymer backbone can be toxic to mammalian cells as they can interact with lipid domains of cell membrane, thus disrupting cell membrane.

In accordance with one or more embodiments of the disclosed subject matter, the structure of the subject guanidinium-functionalized polymers can have a unique balance and distribution of hydrophobicity verses hydrophilicity that promotes self-assembly of the polymer into distinctive nanostructures (e.g., having a size between about 20 and 300 nanometers nm) that substantially reduces the toxicity of the polymers when exposed to mammalian cells. In this regard, the self-assembled nanostructures can have a micelle formation wherein the hydrophobic residuals are located on the inside of the micelle and the hydrophilic residuals located on the surface of the micelle and capable of targeting the pathogens. In particular, based on the balance and distribution of the hydrophilic guanidinium moiety relative to the hydrophobic butyl that connects the guanidinium moiety to the hydrophobic backbone, the subject guanidinium-functionalized polymers can be configured to self-assemble into theses distinctive nanostructures in aqueous solution with a critical micelle concentration (CMC) less than or equal to a defined CMC threshold. For example, in one or more embodiments the subject guanidinium-functionalized polymers can self-assemble into the distinctive nanostructures in an aqueous solution having a CMC less than or equal to 118 micrograms per liter (µg/mL at 25 degrees Celsius (° C.), atmospheric pressure or greater, such phosphate-buffered saline (PBS), and the like. In this regard, the subject guanidinium-functionalized polymers can self-assemble into the distinctive nanostructures in a physiological environment (e.g., an actual physiological environment and a simulated physiological environment simulated using PBS).

In this regard, the subject guanidinium-functionalized polymers can be configured to self-assemble into the protected dynamic nanostructures (with the hydrophobic residuals buried inside the micelle) in an aqueous solution comprising bacterial cells and mammalian cells. Because the hydrophobic residuals are positioned inside the micelle, the guanidinium-functionalized polymers have minimal interaction with the mammalian cells. However, the antimicrobial efficacy attributed to the bacterial killing kinetic mechanism described above is also enabled due to the exposed cationic guanidinium groups located around the outside of the micelle at concentrations above its CMC. In this regard, the protected nanostructures can be configured to open-up, unwind or otherwise dissemble so as to expose the hydrophobic active groups to the lipid domains of the bacterial membrane in response to the binding of the cationic guanidinium groups to the anionic bacterial membrane. As a result, the polymers translocate through the bacterial membrane and into the cytosol in an extended form wherein both the hydrophobic and guanidinium active groups are exposed to interact with cytosolic materials.

In accordance with one or more embodiments, the subject antimicrobial guanidinium-based polymers can comprise a chemical structure characterized by Structure I:

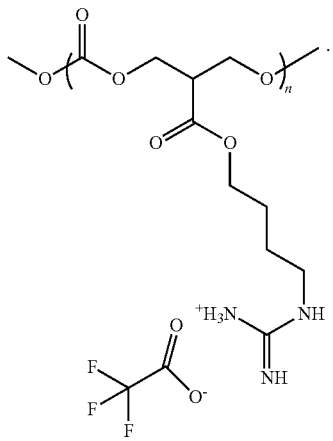

Structure I

In accordance with Structure I, the guanidinium-based antimicrobial polymer comprises a number "n" of repeating monomer units, (referred to herein as guanidinium functionalized monomer units or the monomer units). Each (or in some embodiments one or more) of the monomer units can comprise a polycarbonate group and a cationic guanidinium moiety attached to the polycarbonate group via a butyl group. The number "n" of repeating and connected/bonded guanidinium functionalized monomer units can vary. For example, in some implementations, the number "n" of repeating monomer units can be one or more and one thousand or less. However, in one or more exemplary embodiments, the number "n" of repeating monomer units can be tailored to facilitate formation of the subject guanidinium-based antimicrobial polymers into the protected micelle nanostructures in aqueous solution. In particular, the number "n" of repeating monomer units can be tailored to balance the hydrophobicity of the polymer backbone group and the butyl group relative to the hydrophilicity of the guanidinium moiety to facilitate the self-assembly of the subject polymers into the protected micelle nanostructures, wherein the guanidinium moieties are exposed on the outside of the micelle on the out and the hydrophobic residuals are internalized within a micelle. In this regard, in some embodiments, one or more polymers having Structure I can be configured to self-assemble into the protected micelle nanostructures when "n" is between 5.0 and 65. In another embodiment, one or more polymers having Structure I can be configured to self-assemble into the protected micelle nanostructures when "n" is between 10 and 40. Still in yet another embodiment, one or more polymers having Structure I can be configured to self-assemble into the protected micelle nanostructures when "n" is between 15 and 25.

In the embodiment shown in Structure I, each monomer unit of the polymer backbone includes at least one guanidinium functional group that consists of the cationic guanidinium-based antimicrobial moiety connected to thereto via a butyl spacer group. However, in some implementations, one or more of the monomer units can include no guanidinium functional groups and/or one or more of the monomer units can include two or more guanidinium based functional groups. In this regard, in some implementations, no restriction is placed on the polymer skeletal structure of the skeletal backbone. Exemplary non-limiting polymer skeletal structures can include linear polymers, branched polymers, star polymers, mykto-arm star polymers, latter polymers, cyclic polymers, and graft polymers. The forgoing polymer types can comprise a homopolymer, a random copolymer, or a block copolymer chain. In various exemplary embodiments, the antimicrobial guanidinium based macromolecule is a linear polymer comprising a plurality of covalently bonded guanidinium functionalized monomer units. Herein, a linear polymer has one branch having two peripheral ends (i.e., dangling ends, as the two ends of a segment of a rope). The one branch can comprise one or more polymer chain segments covalently linked together at respective polymer chain ends by way of any suitable linking group, which can include a single bond. Each polymer chain segment of a linear polymer can comprise a homopolymer, random copolymer, or block copolymer chain comprising one or more repeat units. At least one of the polymer chain segments comprises one or more repeat units of the guanidinium functionalized monomer.

In accordance with structure I, the polymer backbone comprises a polycarbonate group. However, in one or more additional embodiments, other hydrophobic polymers can be employed as the polymer backbone. For example, in other embodiments, the polymer backbone can comprise polylysine, polyionene, polyethylenimine and the like.

As shown in Structure I, the antimicrobial guanidinium-moiety is cationic in nature so as to facilitate counterion exchange with anionic phosphate group on the bacterial membranes and change neutralization, thereby facilitating translocation of the resulting nonpolar macromolecule through the bacterial membrane. For example, in the embodiment shown, the guanidinium moiety is characterized by chemical Formula I below:

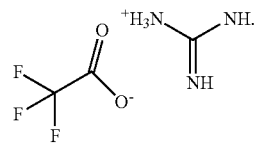

Formula I

In this regard, the antimicrobial guanidinium moiety comprises a hydrosalt of a guanidinium functional group with a positively-charged protonated form of the guanidinium group that is ionically associated with a negatively-charged trifluoroacetic acid (TFA) counterion. However, in some embodiments, the cationic antimicrobial guanidinium moiety can vary. For example, in some embodiments, the cationic guanidinium moiety can comprise a hydrosalt of a guanidine group represented by Formula II below:

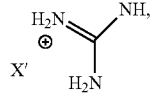

Formula II wherein X' is a negative-charged counterion. In accordance with these embodiments, exemplary negative-charged counterions X' can include but are not limited to: halides (e.g., fluoride, chloride, bromide, iodide), hydroxide, alkyl and aryl carboxylates (e.g., trifluoroacetate, pentafluorobenzoate), hydrogen carbonate, alkyl, and aryl sulfonates (e.g., methane sulfonate, p-toluenesulfonate), methyl sulfate, hydrogen sulfate, nitrate, dihydrogen phosphate, dialkyl and diaryl phosphates, and alkyl and aryl phosphonates.

In various additional embodiments, one or more antimicrobial guanidinium-based polymers described herein that are capable of forming protected nanostructures in aqueous solution can be characterized by Structure II:

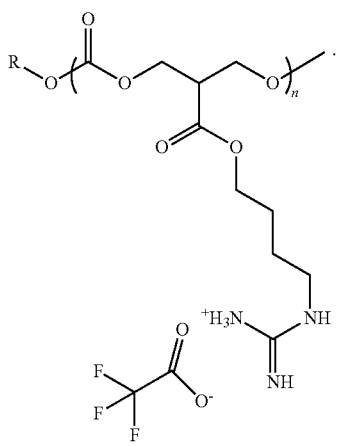

Structure II wherein the variable "R" represents a functional group. In one or more embodiments, the function group "R" can comprise a functional group that facilitates polymerization of the polymer in association with synthesis of the polymer. For example, in one or more embodiments, as discussed in greater detail infra, the subject guanidinium-based polymers comprise polycarbonate backbones and are prepared by organocatalyzed ring opening polymerization (OROP) of a cyclic carbonate (MTC) monomer bearing a pendent protected monomer attached thereto via a butyl group. In this regard, the OROP is facilitated by a nucleophile initiator. Thus, in one or more embodiments, the "R" in Structure II can corresponds to a functional group of a nucleophile initiator of the ROP, such as a protecting functional group of an alcohol. For example, in one or more embodiments, the functional group "R" of Structure II can include but is not limited to, a 4-methylbenzyl alcohol group, a benzyl alcohol group, and the like. For example, in one exemplary embodiment, one or more guanidinium-based polymers described herein can have a chemical structure characterized by Structure III:

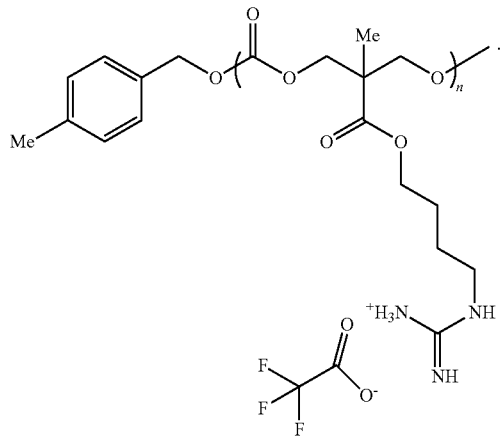

Structure III

In other embodiments, the "R" of Structure II can be or include a carbohydrate moiety (e.g., a sugar), such a saccharide or a monosaccharide (e.g., fructose, galactose, glucose, mannose, etc.).

It should be appreciated that the size of the self-assembled nanostructures formed via the one or more polymers having Structure I, Structure II, Structure III (and the like) can vary depending on the number "n" and composition of the repeating monomer units and possible the "R" functional group. In one or more embodiments, the subject polymers can be configured to form self-assembled nanostructures having a size between about 20 and 300 nm. In another embodiment, subject polymers can be configured to form self-assembled nanostructures having a size between about 100 and 200 nm. Still in yet another embodiment, the subject polymers can be configured to form self-assembled nanostructures having a size between about 150 and 200 nm.

The subject micelle forming guanidinium-based polymers (e.g., having Structure I, Structure II, Structure III, and the like), have shown potent antimicrobial activity against *K. pneumoniae* and various additional clinically-isolated MDR bacteria, including the various ESKAPE pathogens. For example, in addition to *K. pneumoniae*, the subject micelle forming guanidinium-based polymers provide potent antimicrobial activity against both Gram-positive and Gram-negative bacteria, including but not limited to, *Acinetobacter baumannii* (*A. baumannii*), *Escherichia coli* (*E. coli*), *Staphylococcus aureus* (*S. aureus*), methicillin-resistant *S. aureus* (MRSA), and *Pseudomonas aeruginosa* (*P. aeruginosa*), and *Enterococcus faecium* (*E. faecium*). In this regard, one or more example compounds comprising the disclosed micelle forming guanidinium-based polymers were tested in vitro and in vivo (in a lung infection animal model) with substantially greater success over traditional antibiotics (including imipenem, ceftriaxone, and gentamycin, and vancomycin) and alternative guanidinium based polymers that do not have the chemical Structures, I, II, III and the like. In this regard, as compared to commercial antibiotics and similar guanidinium functionalized polymers that include spacer groups other than a butyl group connecting the guanidinium moiety to the polymer backbone, only the subject guanidinium-based polymers self-assemble into unique micelle nanostructures with internalized hydrophobic residuals and decorated by external cationic guanidinium moieties when introduced in an aqueous solution. This unique chemical reaction afforded by the butyl spacer group was found to significantly increase the efficacy and significantly decrease the toxicity of the disclosed polymers relative to traditional antibiotics and alternative guanidinium based polymers that do not have butyl spacer groups between the guanidinium moiety and the polymer backbone.

In particular, as described in greater detail infra with reference to various in vitro and in vivo studies efficacy studies, the subject micelle forming guanidinium-based polymers demonstrated rapid killing kinetics against MDR *K. pneumoniae* as compared to the leading antibiotic imipenem. The subject polymers also showed a low tendency toward medication/antibacterial agent resistance development. Notably, compared to imipenem, the subject polymers demonstrated substantially greater efficacy in an immunocompromised mouse pneumonia model caused by MDR *K. pneumoniae*. In addition, treatment with the subject polymers at the effective dose levels did not induce significant toxicity. Further, as described infra with reference to FIG. 9, relative to alternative guanidinium-based polymers without the self-assembly mechanism afforded by the subject guanidinium-functionalized polymers (e.g., owing to the butyl spacer group), the effective dose (ED) for 50% of infected subjects (e.g., mice) receiving the medication, referred to as the ED50, decreased up to over 50% (e.g., from 3.79 milligrams per kilogram (mg/kg) for comparative polymers having chemical Structure IV discussed infra, to only 1.78 mg/kg for polymers having Structure I). At the same time, the toxicity, measured via lethal dose 50 (LD50) which is the dose that leads to the demise of 50% of the subjects (e.g., mice), also significantly decreased (e.g., from 44.2 mg/kg for Structure IV to 158.0 mg/kg for Structure I, also shown in FIG. 9). As a result, the observed therapeutic window (LD50/ED50) for the disclosed polymers with the butyl spacer groups relative to similar guanidium based polymers without butyl spacer groups increased substantially (e.g., from 11.6 for comparative polymer having Structure IV and 25.1 for comparative polymer having structure V, to 88.8 for the polymer having Structure I. This evidence convincingly distinguishes the subject polymers having Structures I, II, III and the like, as a totally novel class of antimicrobial agents, potentially capable of combating MDR pathogens, including *K. pneumoniae*.

Additionally, the subject guanidinium-based polymers are biocompatible, biodegradable, non-hemolytic, and non-cytotoxic at concentrations above the MIC. The subject guanidinium-based macromolecules are therefore attractive for a wide range of applications ranging from therapeutics to the reduction in the use of antibiotics in agriculture to consumer products, such as for example, cosmetics, skin lotions, and the like. The term biodegradable is defined by the American Society for Testing and Materials (ASTM) as degradation caused by biological activity, especially by enzymatic action, leading to a significant change in the chemical structure of the material. For purposes herein, the subject guanidinium-based polymers having (and variations thereof) can be characterized as biodegradable because they have been shown to undergo at least 60% biodegradation within 180 days, in accordance with ASTM D6400. The subject guanidinium-based macromolecules can also be characterized as enzymatically biodegradable because they have been shown to be degraded (e.g., depolymerized) by a reaction catalyzed by an enzyme. A biocompatible material is defined herein as a material capable of performing with an appropriate host response in a specific application.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 provides a diagram illustrating an example, non-limiting, effective antimicrobial mechanism 100 afforded one or more antimicrobial guanidinium functionalized polymers in accordance with one or more embodiments described herein. Repetitive description of like elements employed in respective embodiments is omitted for sake of brevity.

In this regard, FIG. 1 depicts an interaction between guanidinium functionalized polymers having Structure I, Structure II, Structure III or the like, with a bacteria microbe 124. In particular, FIG. 1 depicts a five step (respectively numbered steps 101-105) process illustrating the antimicrobial mechanism of the subject guanidinium functionalized polymers (having Structure I, Structure II, Structure III or the like). In this regard, when suspended in aqueous solution including bacteria microbes (e.g., bacteria microbe 124) and saline, the subject guanidinium functionalized polymers self-assemble into micelle structures 110. An enlarged illustration of the micelle structure 110 is shown in the call-out box extending therefrom. As shown in the call out-box, the micelle structure 110 comprises a circular structure with the cationic and hydrophilic guanidinium moieties 112 exposed around the external perimeter of the micelle, enclosing or encapsulating the hydrophobic butyl groups 114 and the hydrophobic residuals of the polymer backbone 116. (It should be appreciated that the illustration of the micelle structure is merely exemplary and not drawn with accurate dimensions and arrangements of the actual micelle in practice).

As the polymers come into contact with the bacterial surface at step 101, the cationic guanidinium moieties can be configured to bind with the anionic (negatively charged) phosphate groups on the bacterial surface and experience counterion exchange and charge neutralization. In response to the binding of the cationic guanidinium moieties to the bacterial surface, at 102, the micelle structure 110 unwinds into an extended or open structure 118, thereby exposing the hydrophobic residuals. In this regard, the polymer essentially unravels and wraps itself around the surface of the bacteria, exposing the hydrophobic residuals. The call-out box extending from the open structure 118 provides and enlarged illustration of the binding of the polymer to the bacterial surface and the opening of the polymer from the micelle structure 110 to the open structure 118.

At 103 the polymers then translocate through the hydrophobic lipid bilayer of the bacterial membrane 120 as a non-polar and substantially hydrophobic species. At 104, the polymers are then released through the bacterial membrane 120 and into the cytosol 122. Then at 105, the polymers attack the bacterial biomolecules within the cytosol, causing local disorder and precipitation within the cytosol, leading to cell apoptosis. Accordingly, the hydrophobic residuals and guanidinium groups of the polymers are highly toxic to bacteria once internalized, leading to cytosol precipitation and subsequent cell apoptosis.

Figure 2A:
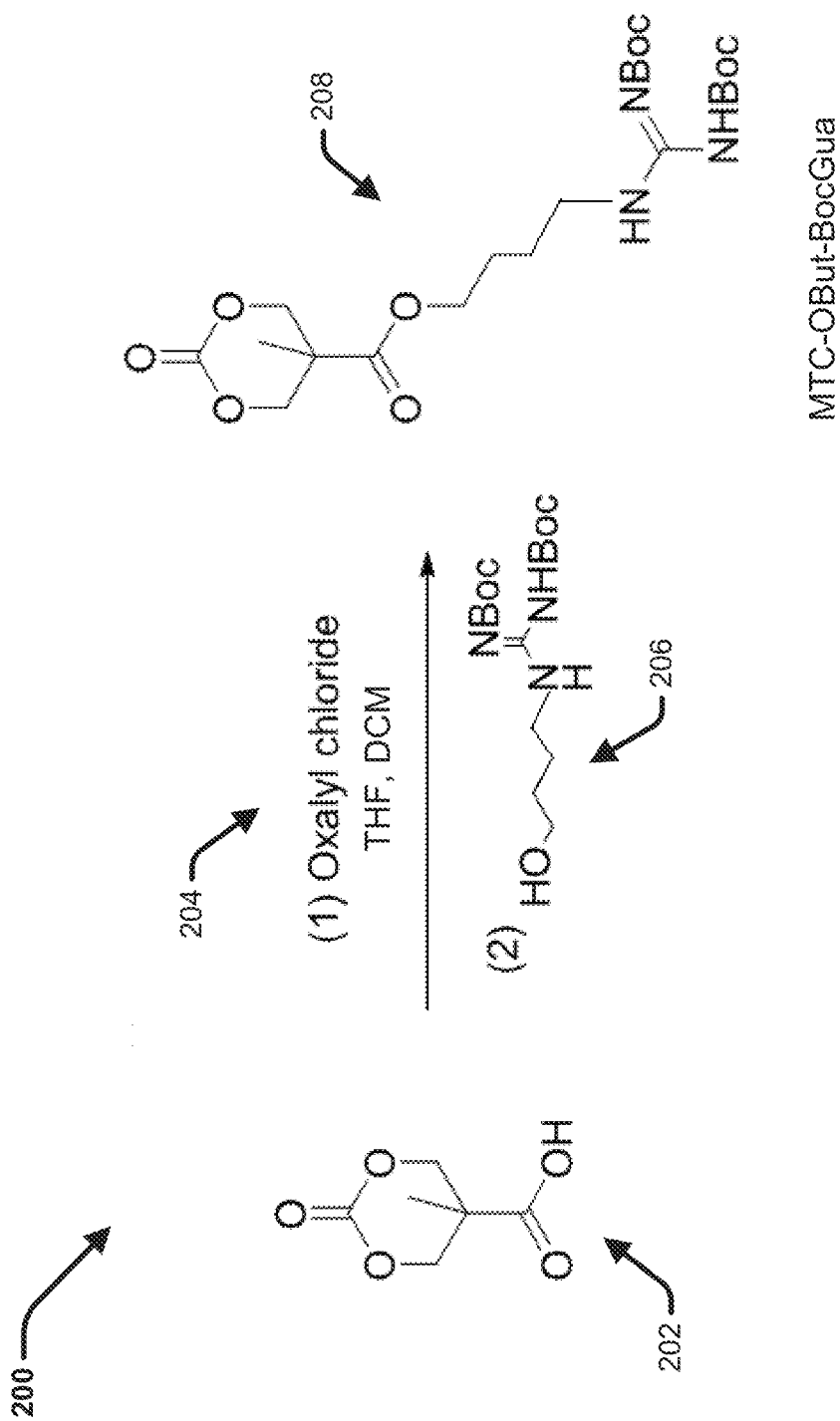
FIG. 2A illustrates a diagram of an example, non-limiting synthesis scheme that can facilitate generation of one or more guanidinium monomers in accordance with one or more embodiments described herein.

FIG. 2A illustrates a diagram of an example, non-limiting synthesis scheme 300 that can facilitate generation of one or more guanidinium functionalized monomers in accordance with one or more embodiments described herein. The one or more guanidinium functionalized monomers generated via synthesis scheme 200 can be further polymerized to generate one or more of antimicrobial guanidinium polymers in accordance with one or more embodiments described herein. For example, synthesis scheme 200 can be employed to produce one or more guanidinium functionalized monomers that can be used to generate one or more antimicrobial polymers characterized by Structure I, Structure II, Structure III and the like. Repetitive description of like elements employed in other embodiments described herein is omitted for sake of brevity.

In the embodiment shown, the resulting guanidinium functionalized monomer having Structure 208 is referred to herein as MTC-OBut-BocGua. The guanidinium functionalized monomer MTC-OBut-BocGua, comprises a cyclic carbonate (e.g., MTC) with a protected guanidinium functional moiety covalently bonded thereto via a butyl spacer group. In this regard, the guanidinium moiety comprises two protecting tert-butyloxycarbonyl (tBoc or Boc) groups. The Boc groups can correspond to independent acid-liable protecting groups. Although the protecting groups of Structure 308 are Boc groups, other suitable protecting groups can be employed, such as but not limited to, benzyloxycarbonyl (Bnoc), and fluorenyloxycarbonyl (Fmoc).

In accordance with synthesis scheme 200 the MTC-OBut-BocGua monomer can be prepared by reacting one or more cyclic carbonates having Structure 202 with one or more protected guanidinium compounds having Structure 206 (e.g., at a molar ratio of about 1:1), using a suitable amount (e.g., a molar ratio of about 1.5:1) of reagents 204 to Structure 202, including oxalyl chloride, tetrahydrofuran (THF) and a solvent (e.g., methylene chloride ($CH_2CL_2$), also identified as (DCM)).

A detailed protocol for the synthesis of MTC-OBut-BocGua monomer in accordance with synthesis schemed 200 using 4-amino-1-butanol as the starting reagent is described as a representative example. Initially, synthesis of Boc-protected guanylated alcohol (HO-But-BocGua) was performed as follows: To a solution mixture of 4-amino-1-butanol (2.1 milliliters (mL), 22.32 millimoles (mmol)) and N,N-diisopropylethylamine (6.0 mL, 34.34 mmol) was added 1,3-bis(tert-butoxycarbonyl)-2-methyl-2-thiopseudourea (3.3 g, 11.16 mmol) in 20 mL of dry $CH_2Cl_2$, and the mixture was left to stir overnight at room temperature. Upon reaction completion, a constant stream of nitrogen gas was bubbled through the reaction mixture for approximately 1.0 hour so as to aid in purging of the gaseous by-product, MeSH. After the removal of residual solvent in vacuo, the crude product was purified by flash column chromatography using silica gel and a hexane-ethyl acetate solvent system as the eluent (gradient elution up to 50% volume (vol.). ethyl acetate) to yield the Boc-protected guanylated alcohol (HO-But-BocGua) as a white solid (3.32 g, 90% yield). The results of a proton nuclear magnetic resonance ($^1$H NMR) study of the HO-But-BocGua at 400 megahertz (MHz), in deuterated chloroform ($CDCl_3$) at 22 degrees Celsius (° C.) were as follows: δ 11.47 (s, 1H, NH), 8.38 (s, 1H, NH), 3.67 (t, 2H, $HOCH_2$—), 3.44 (dd, 2H, —$CH_2N$—), 1.61 (m, 4H, —$CH_2CH_2$—), 1.48 (d, 18H, Boc-$CH_3$).

Thereafter, the synthesis of MTC-OBut-BocGua was performed as follows: In a dry three-neck circular bottom flask equipped with a stir bar, MTC-OH (1.72 g, 10.75 mmol) was dissolved in dry THF (50 mL) with 3-4 drops of DMF. A solution of oxalyl chloride (1.37 mL, 15.87 mmol) in THF (50 mL) was subsequently added from a dropping funnel. Under a $N_2$ gas atmosphere, the solution was stirred for 1.0 hour, after which volatiles were removed under vacuum, yielding an intermediate product MTC-Cl as an off-white solid. The solid was heated to 60° C. for 2-3 minutes to remove any residual solvent, and then re-dissolved in dry $CH_2Cl_2$ (50 mL) and cooled down to 0° C. via an ice bath. A mixture of HO-But-BocGua, 3.28 g, 9.91 mmol) and pyridine (0.87 mL, 10.75 mmol) dissolved in dry $CH_2Cl_2$ (50 mL) was then added dropwise over a duration of 30 minutes, and allowed to stir at 0° C. for an additional 30 minutes before leaving it at ambient temperature for further stirring overnight. After removal of solvent, the crude product was subjected to purification by flash column chromatography using silica gel and a hexane-ethyl acetate solvent system as the eluent (gradient elution up to 80% vol. ethyl acetate) to yield MTC-OBut-BocGua as a white solid (75% yield). The $^1$H-NMR (400 MHz, $CDCl_3$, 22° C.) was as follows: δ 11.44 (s, 1H, NH), 8.30 (t, 1H, NH), 4.64 (d, 2H, $MTC-CH_2$—), 4.20-4.14 (m, 4H, $MTC-CH_2$— and —$OCH_2$—), 3.40 (dd, 2H, —$CH_2N$—), 1.68 (dd, 2H, —$CH_2$—), 1.63-1.57 (m, 2H, —$CH_2$—), 1.44 (s, 18H, Boc-$CH_3$), 1.28 (s, 3H, $MTC-CH_3$).

While one or more particular reactants (e.g., cyclic carbonate having Structure 202, protected guanidinium compounds having Structure 206, etc.), reagents, and/or solvents are depicted; additional embodiments of synthesis scheme 200 are also envisaged. For example, the principal mechanisms of synthesis scheme 200 can be applied to various carbonate based homopolymers, polylysine based homopolymers, polyionene based homopolymers, polyethylenimine based homopolymers, and the like, in accordance with the various features described herein.

Figure 2B:
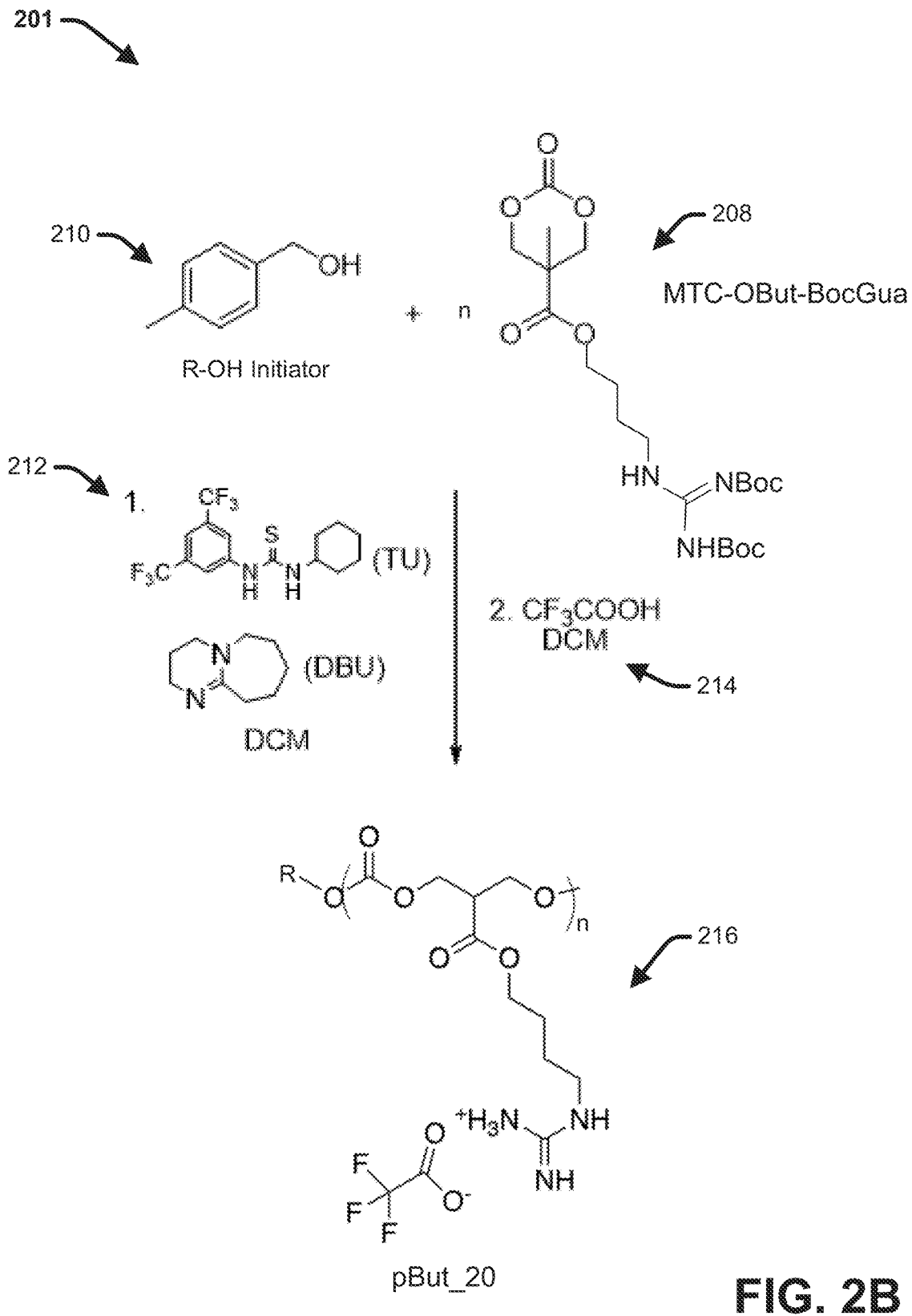
FIG. 2B illustrates a diagram of an example, non-limiting synthesis scheme that can facilitate generation of one or more guanidinium polymers in accordance with one or more embodiments described herein.

FIG. 2B illustrates a diagram of an example, non-limiting synthesis scheme 201 that can facilitate generation of one or more antimicrobial guanidinium polymers in accordance with one or more embodiments described herein. In this regard, synthesis scheme 201 can be employed to produce one or more antimicrobial polymers characterized by Structure I, Structure II, Structure III, and the like. Repetitive description of like elements employed in other embodiments described herein is omitted for sake of brevity.

Synthesis scheme 201 particularly exemplifies the generation of one or more antimicrobial guanidinium polymers prepared by OROP of one or more guanidinium functionalized monomers MTC-OBut-BocGua having Structure 208. In the embodiment shown, the number of monomers "n" can be precisely controlled as a function of the concentration or amount MTC-OBut-BocGua employed. In accordance with synthesis scheme 201, the OROP of MTC-OBut-BocGua can be performed using a nucleophile having a protected alcohol group with structure R—OH as the initiator, wherein "R" the corresponds to the one or more suitable functional groups described herein. For example, in the embodiment shown, the structure 210, representing (4-methylbenzyl alcohol) is provided as an example initiator.

In accordance with synthesis scheme 201, the MTC-OBut-BocGua can be polymerized using OROP in accordance with a two-step procedure to generate the resulting guanidinium functionalized polymer having structure 216, (which corresponds to Structure II above and also referred to herein as pBut_20). In this regard, at 212, the first step comprises polymerizing the MTC-OBut-BocGua in a solvent (e.g., DCM) using the R—OH initiator and a defined amount of reagents, including an organo-catalyst (e.g. 1,8-Diazabicyclo[5,4,0]-undec-7-ene (DBU)), N-(3,5 trifluoromethyl)phenyl-N-cyclohexylthiourea (TU), or DBU/TU), and optionally, an accelerator. In one or more embodiment, the amount of organo-catalyst employed relative to the amount of MTC-OBut-BocGua is (1:10). For example, due to the inherent nature of the subject polymers with the butyl attached guanidinium moieties to form the disclosed nanostructures in aqueous solution, the amount of organ-catalyst employed in order to fully polymerize the subject polymers to a desired length can be at least 1:10 molar ratio with respect to the monomer. The result of the first step at 212 produces an intermediate protected homopolymer (not shown) that corresponds to Structure 216 yet having one or more Boc protecting groups associated with the guanidinium moiety. The second step at 214 comprises subsequently deprotecting the intermediate protected homopolymer in DCM using a protic acid (e.g., trifluoroacetic acid (TFA) or another suitable protic acid) to form the antimicrobial polymer having Structure 216 bearing the pendent cationic guanidinium moieties with the negatively charged counterion (e.g., TFA$^-$ in the embodiment shown). For example, the protic acid can have one or more protons, which can be donated to forma a hydrosalt of guanidine.

The detailed procedures for the synthesis of Structure 216 (also referred to herein as pBut_20) in accordance with synthesis scheme 201 via ring-opening polymerization (ROP) of MTC-OBut-BocGua with 4-methyl benzyl alcohol as the initiator are given as a representative example. In this regard, in a glove box, MTC-OBut-BocGua (0.398, 0.84 mmol), 4-methyl benzyl alcohol (4.36 mg, 0.035 mmol) and TU (31.08 mg, 0.084 mmol) were dissolved in dry DCM (2 mL). Then, DBU (12.6 μL, 0.084 mmol) was added to initiate the polymerization and the solution was left to stir for 3 hours before the reaction was stopped by quenching the catalyst using an excess of benzoic acid (11 mg, 0.09 mmol). The crude polymer was isolated and purified via preparative size-exclusion chromatography using THF as the eluent. Upon removal of the solvent in vacuo, a transparent white solid was obtained as the product, P(MTC-OBut-BocGua)_20 (72% yield). PDI: 1.28. $^1$H-NMR (400 MHz, CDCl$_3$, 22° C.): δ 11.50 (s, 18H, NH), 8.36 (bs, 18H, NH), 5.09 (s, 2H, initiator —CH$_2$—), 4.29 (m, 66H, MTC-CH$_2$—), 4.14 (m, 35H, —OCH$_2$—), 3.45 (m, 36H, —CH$_2$N—), 2.34 (s, 3H, initiator —CH$_3$), 1.72-1.63 (m, 71H, —CH$_2$CH$_2$—), 1.53-1.41 (d, 363H, Boc-CH$_3$), 1.28-1.18 (bs, 57H, MTC-CH$_3$).

For the removal of the Boc protecting groups, an acid-mediated deprotection strategy was adopted. P(MTC-OBut-BocGua) 20 (150 milligrams (mg)) was dissolved in CH$_2$Cl$_2$ (9.0 mL) and trifluoroacetic acid (1.0 mL). The reaction mixture was sealed and stirred at room temperature for 14-18 hours. After the removal of solvent in vacuo, slightly yellow waxy solid was obtained as the deprotected guanidinium-functionalized polymer in quantitative yields. The polymer was subsequently dissolved in water and lyophilized to yield a white transparent solid, pBut_20. Complete deprotection was ascertained by $^1$H-NMR analysis. The results were as follows: Yield: 81%; $^1$H-NMR (400 MHz, CD$_3$OD, 22° C.): δ 4.30 (m, 61H, MTC-CH$_2$—), 4.18 (m, 36H, —OCH$_2$—), 3.22 (m, 36H, —CH$_2$N—), 1.77-1.64 (m, 69H, —CH$_2$CH$_2$—), 1.23 (bs, 53H, —CH$_3$).

Figure 3A:
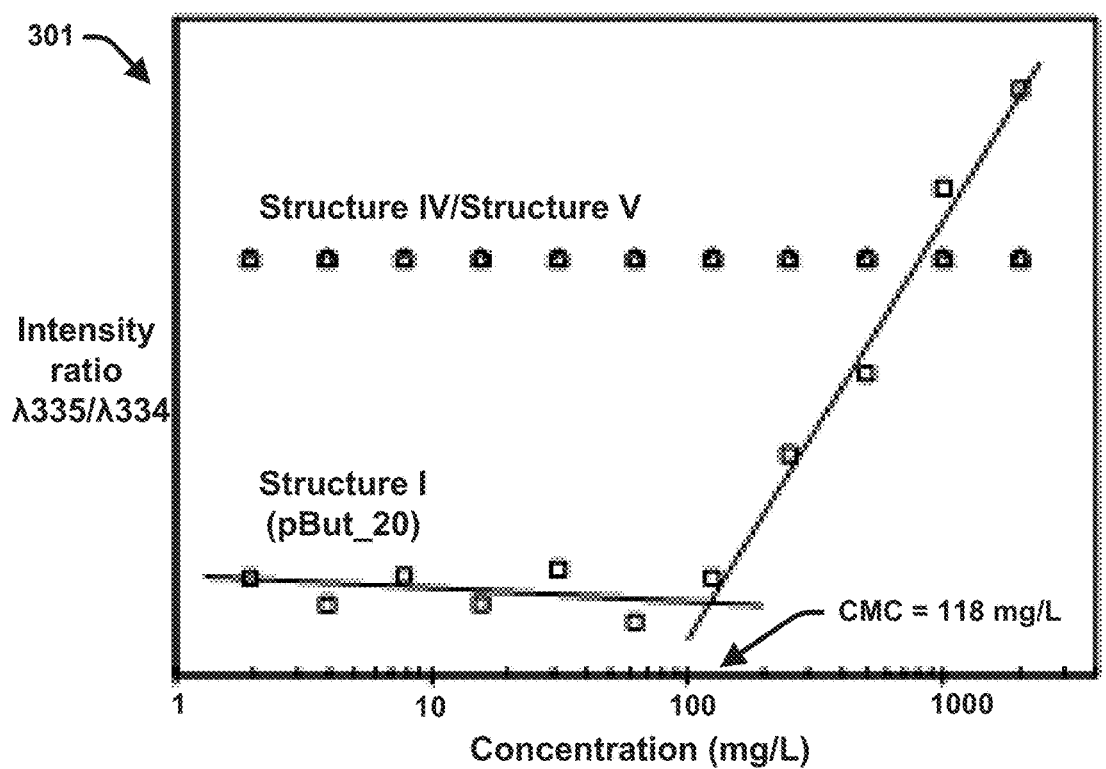
FIG. 3A presents an example, non-limiting graph that demonstrates self-assembly of one or more guanidinium-functionalized polymers in accordance with one or more embodiments described herein.
Figure 3B:
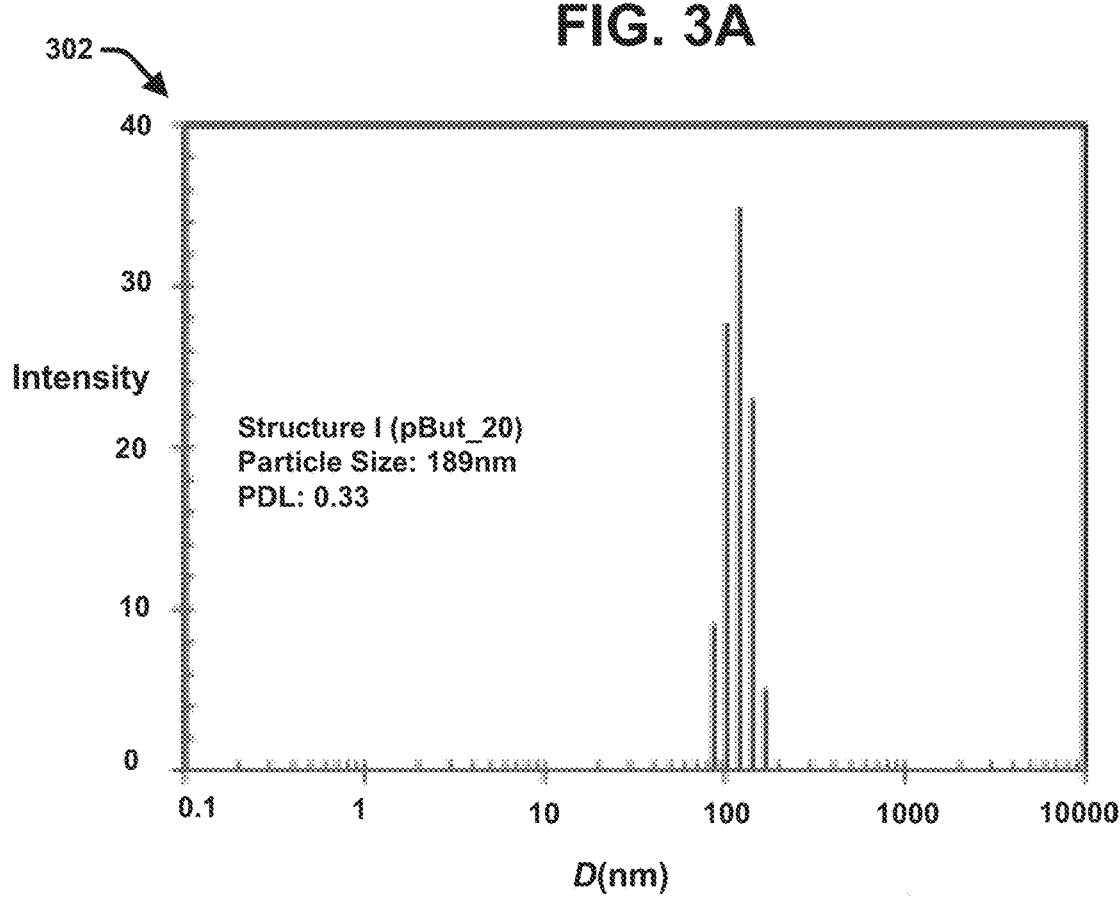
FIG. 3B presents an example, non-limiting chart demonstrating critical micelle concentration (CMC) values of one or more guanidinium-functionalized polymers in accordance with one or more embodiments described herein.
Figure 3C:
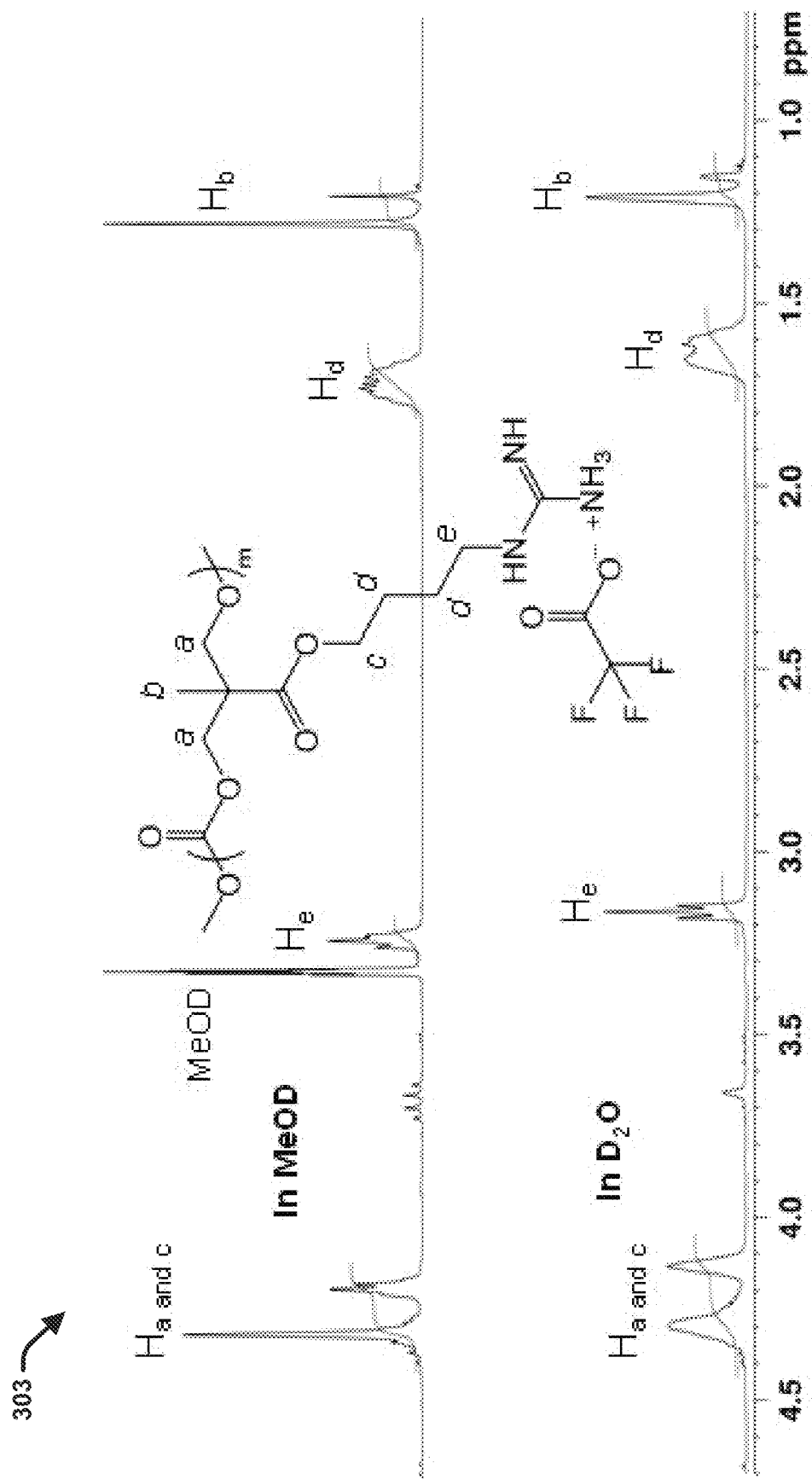
FIG. 3C presents a graph illustrating the results the proton nuclear magnetic resonance spectra of one or more guanidinium-functionalized polymers in accordance with one or more embodiments described herein.

The self-assembly behavior of the polyguanidinium polymers having Structure I the like, (e.g., pBut_20), in aqueous solution was investigated by determining their critical micelle concentrations (CMCs) and particle sizes in PBS buffer solution, as well as the changes of proton NMR spectra of the polymer in MeOD and D$_2$O. The results are shown in FIGS. 3A-3C. To facilitate comparison, two highly similar antimicrobial guanidinium-functionalized polymers without having the butyl spacer group of Structure I were also tested. In this regard, the comparison polymers tested respectively have Structures IV and V below:

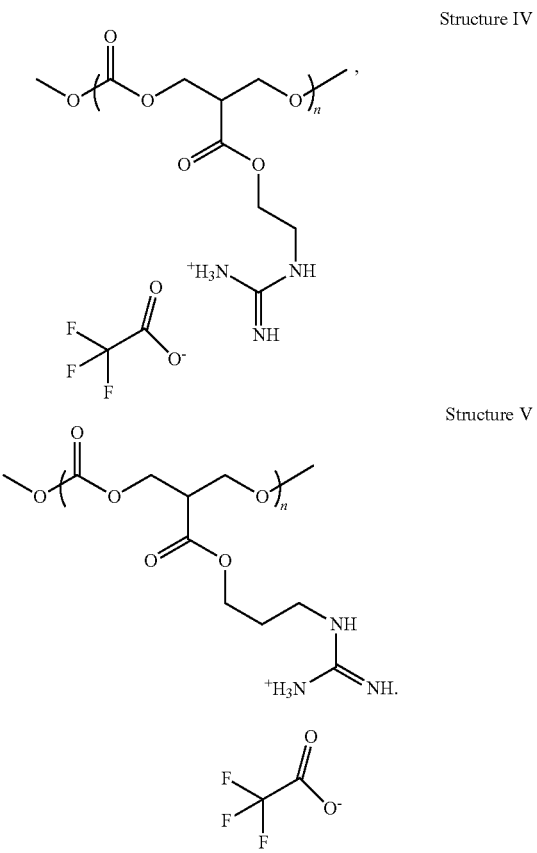

It is important to note that the comparison Structures IV and V differ from Structure I only with respect to the spacer group that connects the cationic guanidinium moiety to the polycarbonate polymer backbone unit. In this regard, instead of a butyl group, Structure IV comprises an ethyl spacer group and Structure V comprises a propyl spacer group. However, as demonstrated below, although the difference between Structures I and IV or Structures I and V appears to be only a slight change to the chemical structure of the spacer group, this slight change has been found to provide remarkable and unexpected differences in the physical structure and antimicrobial properties of the subject guanidinium based polymers when provided in aqueous solution with a CMC of 118 mg/L. As described herein, these markedly improved antimicrobial properties are attributed to the unique and unexpected chemical/structural nature of the guanidinium functionalized polymers having the butyl spacer group (Structure I) to form the disclosed micelle nanostructures.

In this regard, FIG. 3A presents an example, non-limiting graph 301 that demonstrates self-assembly of one or more guanidinium-functionalized polymers having Structure I (e.g., Dp_20) in accordance with one or more embodiments described herein. In accordance with graph 301, the CMC values were determined from plot of intensity ratios λ335/λ334 from fluorescence spectra of pyrene in PBS buffer at 25° C. FIG. 3B presents an example, non-limiting chart 302 demonstrating critical micelle concentration (CMC) values of one or more guanidinium-functionalized polymers having Structure I (e.g., Dp_20) in accordance with one or more embodiments described herein. In accordance with graph 302, the DLS size distribution of pBut_20 was determined in PBS buffer (1.0 µg/mL). FIG. 3C presents an example graph 303 illustrating the results of the $^1$H NMR spectra of pBut_20 in MeOD and $D_2O$, in accordance with one or more embodiments described herein.

With reference to FIGS. 3A-3D, as shown in graph 301, it was clearly observed that polymers having Structure I (e.g., Dp_20), formed micelles in PBS buffer and its CMC value is 118 mg/L. In contrast, comparative guanidinium functionalized polymers without butyl spacer groups having Structures IV and V respectively, did not form micelles under the same conditions. This result indicates that increasing the length of the hydrophobic alkyl spacer significantly enhanced the overall hydrophobicity of the polymer, leading to the formation of the micelles. The micelles formed from Structure I shielded the hydrophobic domain of the polymer in the micellar core, which is helpful to lessen toxicity upon in vitro injection. As shown in graph 302, the mean diameter of the micelles was determined to be 189 nm in PBS buffer with a single size distribution (polydispersity index: 0.33). As shown in graph 303, the formation of the micelles from polymers having Structure I (e.g., pBut_20) in aqueous solution was also confirmed by analysis of the proton NMR. As compared to the spectrum of pBut_20 in MeOD, the peaks of the protons on the carbonate backbone (H-a) and those of the hydrophobic alkyl groups (H-b, H-c and H-d) were broadened in $D_2O$ due to the restricted movement of the molecules in the micelles.

Figure 8:
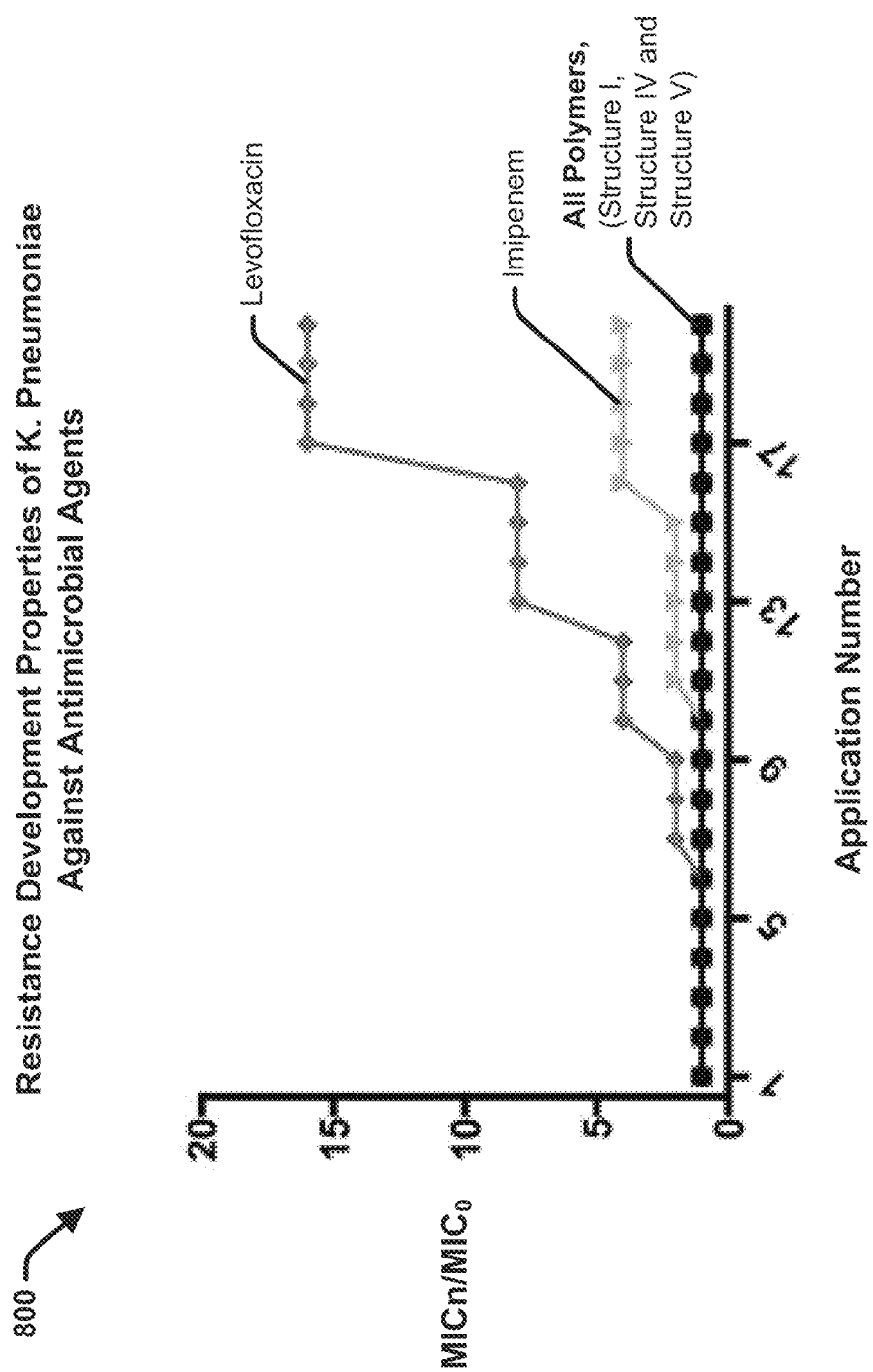
FIG. 8 illustrates an example, non-limiting graph that demonstrates antibiotic resistance development properties of *K. pneumoniae* against one or more antimicrobial guanidinium polymers in accordance with one or more embodiments described herein.

The guanidinium-based polymers disclosed herein having Structures I, II, III and the like have demonstrated strong efficacy as antimicrobial agents against both Gram-negative and Gram-positive microbes, including MDR microbes, such as but not limited to: *K pneumoniae, A. baumannii, E. coli, S. aureus*, MRSA, and *P. aeruginosa*. For example, with respect to MDR *K. pneumonia*, the subject guanidinium-based polymers have also demonstrated high efficacy (e.g., a 100% bacterial apoptosis rate) at relatively low minimum inhibitory concentration MIC. In this regard, the MIC value at which 100% of the *K. pneumoniae* bacterial growth was inhibited (referred to as MIC100), was only 8 parts per million (ppm) in milligrams per liter (mg/L) against 4 out of 25 clinically isolated MDR *K. pneumoniae* strains, 16 mg/L against 11 out of 25 strains, 32 mg/L against 5 out of 25 strains, and 64 mg/L against 5 out of 25 strains (as shown in FIG. 5 below). In addition, the MIC100 concentrations for various different strains of the aforementioned Gram-negative and Gram-positive bacteria ranged between only 4.0 ppm and 16.0 ppm (measured in mg/L) as shown in FIG. 4. In addition, the subject guanidinium based polymers having Structures I, II, III and the like, demonstrated low effective dose amounts against *K. pneumoniae* 9170 in vivo, demonstrated by an ED50 of less than 2.0 mg/kg and an ED95 less than 8.5 mg/kg), while further demonstrating extremely low toxicity, demonstrated by an LD50 of 158.0 mg/kilogram (mg/kg) and an LD5 of 141.8 mg/kg, respectively. In this regard, the subject guanidinium-based polymers exhibited a therapeutic index (measured as LD50/ED5) of almost 90, which is extremely high. The subject guanidinium based polymers also demonstrated rapid kill-times relative to imipenem (e.g., at only about 75 minutes as opposed to more than 180 minutes to kill 99.9% of MDR *K. pneumoniae*, i.e. 3 log reduction in the bacterial counts), which was shortened significantly (e.g., 30 minutes and 15 minutes, respectively) with dosage increases of 2× and 4× (a shown in FIG. 6 infra). Unlike antibiotics, the subject guanidinium-based polymers further exhibited strong immunity to development of medication/antibacterial agent resistance (demonstrated by no change in MIC after 20 repeat administrations at sub-lethal dosage amounts), as shown in FIG. 8 infa.

In this regard, the efficacy, killing kinetics, toxicity and medication/antibacterial agent resistance development characteristics of the subject guanidinium-based polymers having Structure I was tested in vitro and in vivo (e.g., in a mouse model), against clinically isolated bacterial strains, including MDR *K. pneumoniae, A. baumannii, E. coli, P. aeruginousa, E. faecium*, and MRSA strains. All isolates were identified by routine laboratory methods and stored in 20% (v/v) glycerol at −80° C. The MDR clinical isolates were obtained from patients' blood and phlegm. To facilitate comparison, the similar antimicrobial guanidinium-functionalized polymers having Structure IV and Structure V respectively (e.g., without having the butyl spacer group of Structure I) were also tested.

The efficacy, killing kinetics, toxicity, and medication/antibacterial agent resistance development characteristics of the subject guanidinium based polymers having Structures I, IV, and V were also tested against the clinically isolated pathogens in comparison to various commercial antibiotics, including imipenem, vancomycin, ceftriaxone, and gentamycin). The in vitro tests are described with reference to FIGS. 4-8, and the in vivo tests are described with reference to FIGS. 9-11.

In this regard, FIGS. 4 and 5 respectively illustrate the MICs of guanidinium functionalized polymers having Structures I, IV and V and antibiotics (ceftriaxone, gentamycin, imipenem, and vancomycin) against the clinical isolates mentioned above. The MICs of the guanidinium functionalized polymers and the respective antibiotics against the clinical isolates were measured via the broth microdilution method. In accordance with the broth microdilution method, the MDR microbes including one or more strains of *K. pneumoniae, E. coli, A. baumannii, P. aeruginosa, E. coli, E. faecium*, and MRSA were harvested in mid exponential growth phase after grown overnight in Mueller-Hinton (MH) agar plates at 37° C. The antimicrobial agents were prepared in MH broth (MHB) at various concentrations. The bacteria suspensions were then diluted with phosphate-buffer saline (PBS, PH 7.4) to adjust the turbidity approximately to the Standard McFarland 0.6, which corresponds to the concentration of $1\times10^8$ colony-forming unit (CFU/mL), after which the bacteria suspension was further diluted by 100-fold with MHB ($1\times10^6$ CFU/mL). Subsequently, equal volumes (100 microliters (µL)) of bacterial suspension and agent solution prepared previously were mixed in each well of a 96-well plate and incubated for 18 h at 37° C. Broth containing bacteria alone was employed as the negative control, and each MIC was tested in triplicate. The results are presented in FIGS. 4 and 5.

In this regard, FIG. 4 presents an example, non-limiting table 400 comparing the MIC values (measured in mg/L) of the tested antimicrobial agents against various different types and strains of MDR clinically isolated bacterial. The MIC values reported via table 400 respectively represent the lowest concentration of the tested antimicrobial agents at which no visible turbidity was observed with unaided eyes, or 100% bacterial growth inhibition. To facilitate comparison, imipenem and vancomycin, typical first-line therapies against Gram-negative and Gram-positive pathogens, were employed as standards or control antibiotics. Unlike the control antibiotics, the three different guanidinium functional polycarbonates respectively exhibited a broad-spectrum of antibacterial activity against both Gram-negative and Gram-positive strains. In this regard, imipenem only demonstrated efficacy against the Gram-negative strains (e.g., the *K. pneumoniae* (K.P.), *E. coli* (E.C.), and *A. baumannii* (A.B.) strains), and vancomycin only demonstrated efficacy against Gram-positive strains (e.g., E. *Faecium* (E.F.) and the methicillin-resistant *S. aureus* (MSRA) strains). In addition, the respective guanidinium functionalized polymers exhibited relatively low MIC values across the board, ranging from 4.0 to 64.0 mg/L. However, relative to Structure IV and Structure V, the majority of these bacteria were more susceptible to the disclosed subject guanidinium functionalized polymers having Structure I with the longer butyl spacer.

FIG. 5 presents an example, non-limiting table 500 providing the cumulative distribution of MIC values (in mg/mL) for the three guanidinium functionalized polymers respectively having Structures I, IV, and V, as well as antibiotics ceftriaxone, gentamycin, and imipenem, against 25 clinical isolates of MDR *K pneumoniae*. The MIC values reported via table 500 respectively represent the lowest concentration of the tested antimicrobial agents at which no visible turbidity was observed with unaided eyes, or 100% bacterial growth inhibition. The MIC values, measured range from 1.0 mg/mL to 512 mg/mL (e.g., exponentially increased), and are presented at the top of table 500 along the x-axis. The values provided within the respective cells of table 500 and correspond to different degrees (e.g., percentages) of bacterial growth inhibition observed at the respective MIC values. In this regard, a value of 100 for Structure I corresponds to 100% bacterial strains (i.e. 25 out of 25 strains) which have the particular MIC value (64 mg/mL) or below, a value of 80 corresponds to 80% bacterial strains (i.e. 20 out of 25 strains) which have the particular MIC value (32 mg/mL) or below, a value of 60 corresponds to 60% bacterial strains (i.e. 15 out of 25 strains) which have the particular MIC value (16 mg/mL) or below, and so on.

As shown in table 500, to inhibit the growth of 25 MDR *K. pneumoniae* strains, 512, 256 and 64 mg/mL is needed for Structure IV polymers, Structure V polymers, and Structure I polymers, respectively. In this regard, the guanidinium functionalized polymers having Structure I demonstrated significantly superior in vitro antimicrobial efficacy relative to ceftriaxone, gentamycin and imipenem. Moreover, consistent with Table 400, the results presented in table 500 show that the guanidinium functionalized polymer having Structure I is substantially more potent than the comparative guanidinium functionalized polymers having Structures IV and V against clinically isolated MDR *K. pneumoniae* strains.

In addition to the in vitro MIC studies discussed above, an in vitro time-killing assay was employed to understand the bactericidal activity of the subject guanidinium functionalized polymers having Structure I against *K. pneumoniae* 9170. The time killing assay compared the in vitro killing activity verses time of guanidinium functionalized polymers having Structure I with the alternative guanidinium functionalized polymers having Structures IV and Structure V, as well as imipenem. In accordance with the time-kill assay, the bacteria were suspended in MHB to achieve a final concentration of 1×10$^6$ CFU/ml. Then the sample was treated with polymers and imipenem at concentrations of 1×, 2×, and 4×MIC for 30, 60, 90, 120, 150, and 180 minutes. At these time points, the samples were pipetted out and further diluted with different dilution factors. Finally, 50 µL of each diluted solution was plated on a MH agar plate and incubated for 24 hours at 37° C. An untreated inoculum group was also employed as a negative control. Each test was carried out in triplicates and the results were measured as mean log 10 (lg) (CFU/mL)±standard deviation (SD). The results are presented in FIGS. 6A and 6B.

Figure 6A:
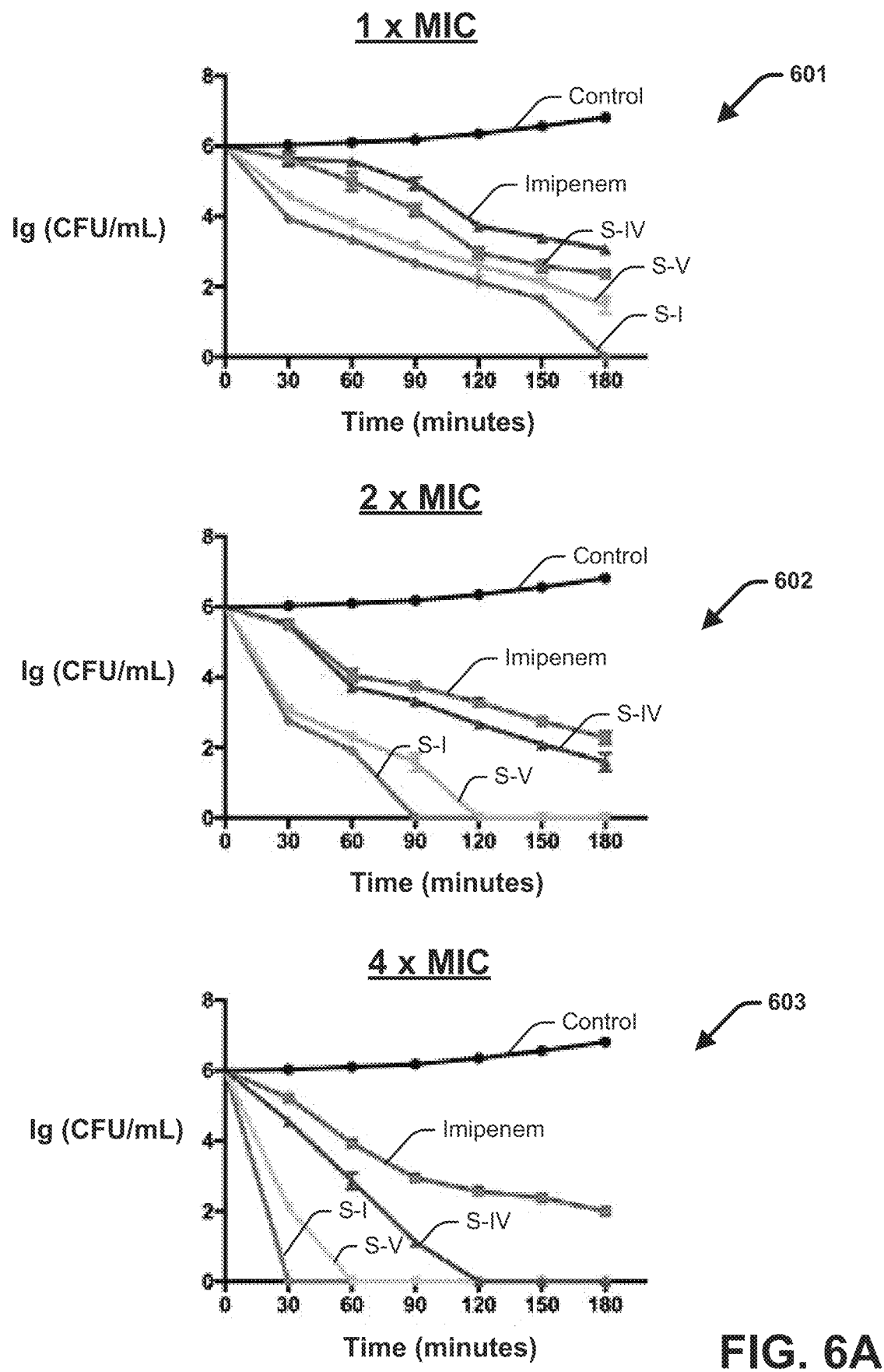
FIGS. 6A and 6B present graphs respectively representing the in vitro killing kinetics of the subject antimicrobial guanidinium polymers against clinically isolated, MDR *K. pneumoniae* in accordance with one or more embodiments described herein FIG. 7 provides a graph illustrating the cytosolic material leakage from *K. pneumoniae* in response to treatment with one or more antimicrobial guanidinium polymers in accordance with one or more embodiments described herein.
Figure 6B:
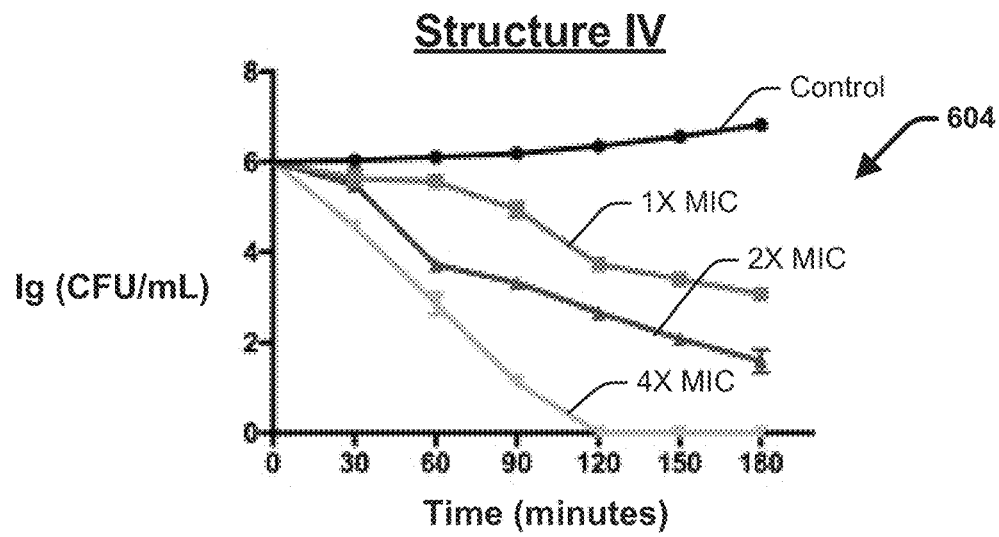
Figure 6B:
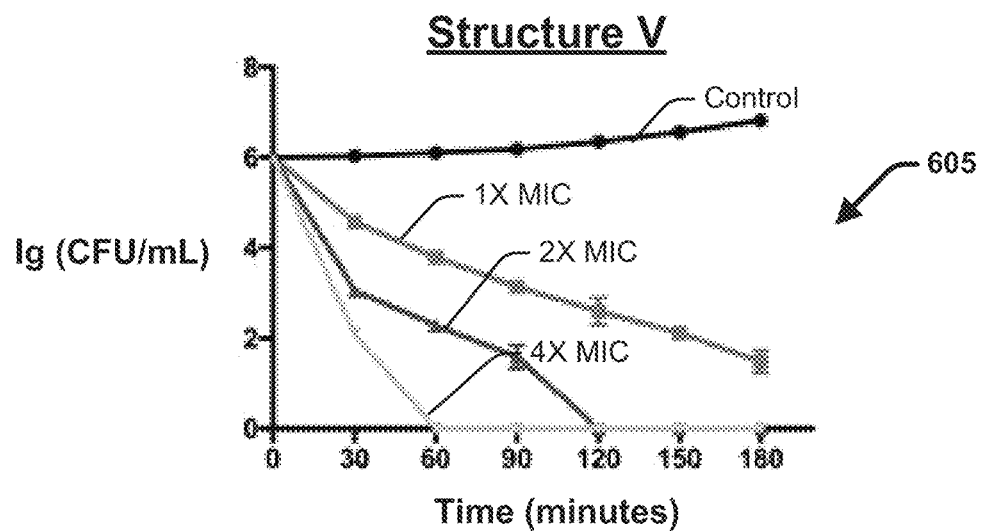
Figure 6B:
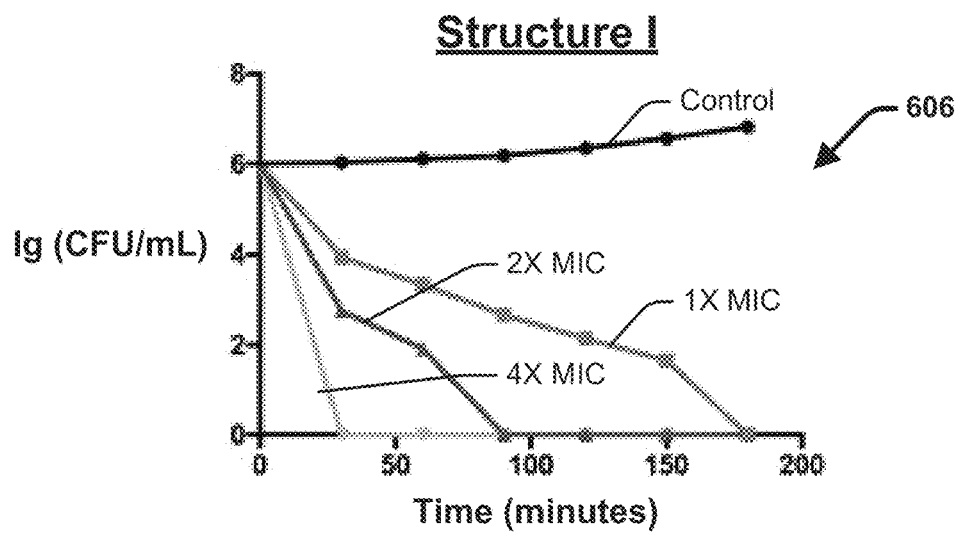

FIG. 6A presents charts 601, 602, and 603, which respectively depict time to kill curves the tested antimicrobials and negative control at different MIC concentrations. FIG. 6B presents charts 604, 605, and 606 which respectively depict changes in CFU (measured in mean lg (CFU/mL)±SD) for polymer having Structure IV (chart 604), polymer having Structure V (chart 605), and polymer having Structure I (chart 606). As shown in FIGS. 6A and 6B, each of the respective polymers having Structure I (S-I), Structure IV (S-IV), and Structure V (S-V), respectively displayed a dose-dependent bactericidal effect, while the activity of imipenem was independent of dose. Taken as a group, the respective polymers showed favorable kinetics to imipenem. For example, at 2×MIC concentration, for imipenem, S-IV, S-V, and S-I, it took 180 min, 120 min, 30 min and 30 min, respectively, to kill 99.9% bacteria (3 log reduction in bacteria counts). However, in addition to out-performing imipenem, the subject polymers having Structure I (S-1) demonstrated the fastest killing kinetics relative to the other active agents at all MIC concentrations. Notably, after only 2.0 hours of exposure at 4×MIC concentration, each of the polymers completely killed MDR *K. pneumoniae*, whereas viable bacteria were still observed for the imipenem-treated sample. Further, the guanidinium functionalized polymer having Structure-I completely killed the MDR *K. pneumoniae* after only 30 minutes of exposure at 4×MIC, twice as fast as the next comparable polymer having structure V and four times as fast as the polymer having structure IV. These results demonstrate a rapid dose-dependent bactericidal effect for the subject guanidinium functionalized polymers with butyl spacer groups having Structure I. These remarkable killing efficacy kinetics suggest the ability of the subject guanidinium functionalized polymers having Structure I to restrain not only routine *K. pneumoniae* infections but also shock (e.g., as a result of decreased secretion of endo- and exotoxins) and other complications associated with MDR *K. pneumoniae* infection.

The quantitative cytosolic material leakage study was conducted using the subject guanidinium functionalized polymers in comparison with membrane-lytic antimicrobial polymyxin B and beta-sheet forming antimicrobial peptide IRIKIRIK. In accordance with the cytosolic material leakage study, *K. pneumoniae* 9170 was suspended in PBS to a concentration of 2×10$^9$ CFU/mL. The antimicrobial agents were added to the bacteria suspension at a concentration of ½ MIB, 1×MBC and 2×MBC (MBC, minimum bactericidal concentration at which 99.9% bacterial cells are killed). The untreated bacteria suspension was used as control. All samples were incubated for 2.0 hours at 37° C. After incubation, the samples were filtered with a 0.22 micrometer (µm) filter to separate the bacteria from the supernatant. The supernatant was subsequently measured for its absorbance using the Thermo Scientific NanoDrop 2000 spectrophotometer based on UV absorption at 260 nm. The results are shown in FIG. 7.

Figure 7:
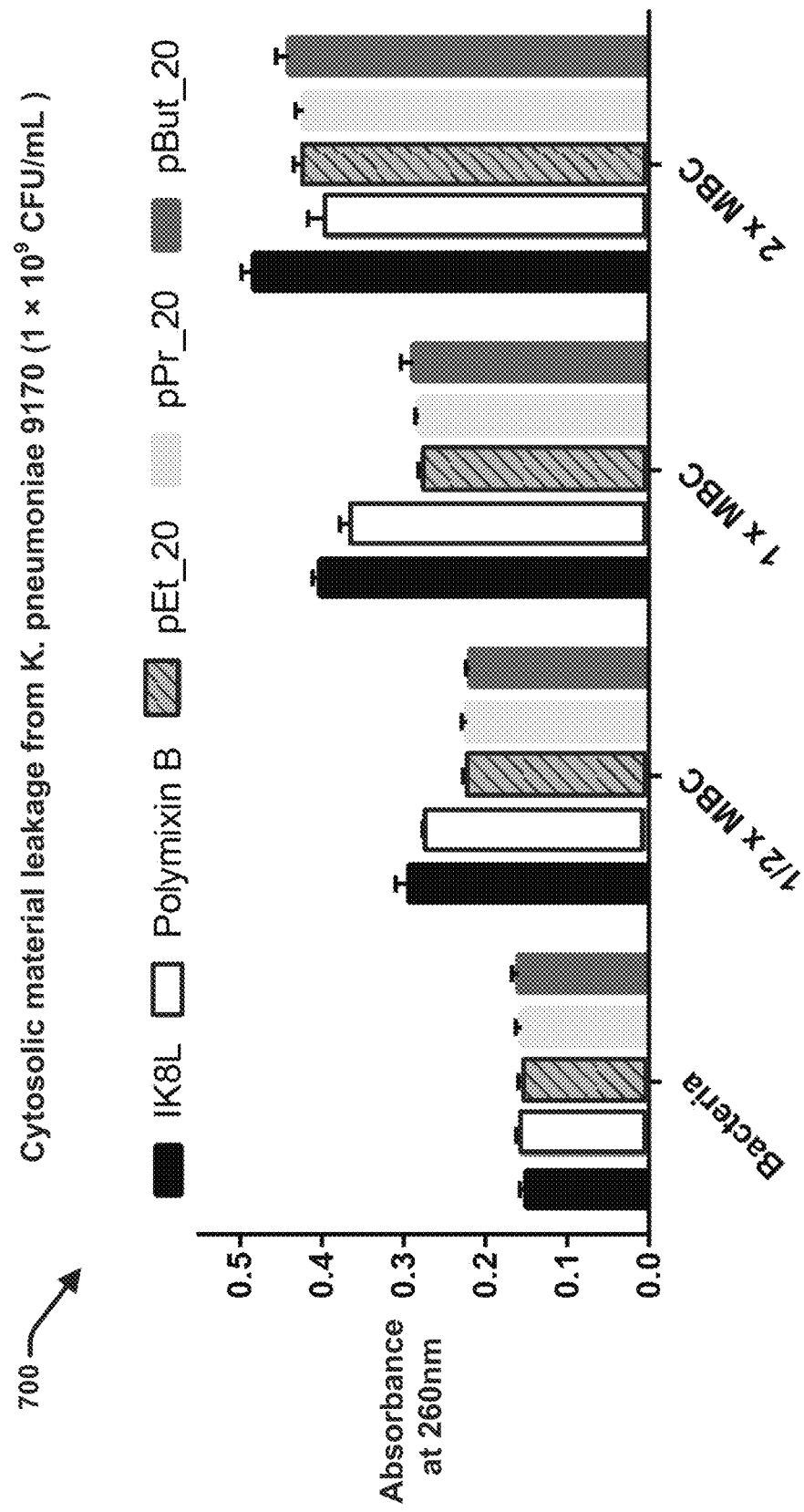

In this regard, FIG. 7 provides a graph 700 illustrating the cytosolic materials leakage from *K. pneumoniae* 9170 after 2.0 hours treatment with the three polymers having Structures I, IV, and V at concentrations of ½ MIB, 1×MBC and 2×MBC. Untreated bacteria suspension was used as control. Compared to the membrane-lytic antimicrobial agents (polymyxin B and beta-sheet forming peptide), the three polymers caused significantly lower leakage of the cytosolic materials at both ½ MBC and 1×MBC. These results indicate that the polymers killed *K. pneumoniae* mainly based on membrane translocation followed by precipitation of cytosolic materials. During membrane translocation, it also causes membrane disruption to a certain degree.

FIG. 8 illustrates an example, non-limiting graph 800 that demonstrates the antibiotic resistance development properties of K. pneumoniae against various antimicrobial agents in accordance with one or more embodiments disclosed herein. In this regard, graph 800 demonstrates the robustness the guanidinium polymers having Structures I, IV and V against the development of antibiotic resistant K. pneumoniae 9170 compared to the commercial antibiotics levofloxacin and imipenem. To test bacterial resistance and resistance prevention, a sub-lethal dose (so as to not kill all bacteria) of the respective antimicrobials was repeatedly applied to K. pneumoniae samples for 24 hours at each passage, wherein the bacteria were allowed to replicate and/or mutate. MIC values of the respective antimicrobials were then measured after each repetition to monitor MIC changes. An increase in MIC value indicates development of resistance in the bacteria. In particular, samples of K. pneumoniae 9170 bacteria were first exposed to the respective antimicrobials (e.g., All polymers having Structures I, IV and V, imipenem and levofloxacin) for the determination of MICs as described above. Subsequently, 50 µL of bacteria from wells of 0.5×MIC were harvested and grown overnight, and then subjected to MIC determination for up to 20 similar serial passages (e.g., 20 single applications once a day for 20 days).

The development of medication/antibacterial agent resistance in K. pneumoniae was monitored by recording the changes in the MIC as shown via graph 800. Unfortunately, antibiotic resistance has raised a global concern over the past few years. However, as shown in graph 800, after serial passaging of K. pneumoniae 9170 at sub-lethal concentrations the MICs of the three polymers against this strain remained constant throughout the entire experiment, while the MICs of levofloxacin and imipenem suddenly increased as much as 2 times by the $7^{th}$ and $11^{th}$ passage, respectively. Moreover, by the $20^{th}$ passage the MIC's of levofloxacin and imipenem increased 16 and 4-fold, respectively. These results demonstrate that the guanidinium functionalized polymers, including the polymers having Structure I as described herein, can effectively prevent resistance development, and thus prove to be beneficial in clinical settings in treating MDR K. pneumoniae infections.

In addition to the in vitro studies discussed above, FIGS. 9-11 demonstrate the antimicrobial efficacy of the subject guanidinium-based macromolecules in treating K. pneumoniae 9170 in vivo. In this regard, the subject guanidinium-based macromolecules having Structure I were tested relative to comparative polymers having Structures IV and V and imipenem in a mouse model. In this regard, immunosuppressed mice (7 weeks old) were used for the following in vivo studies. Immunosuppression was induced by intra-peritoneal injection of 200 mg/kg cyclophosphamide 4 days prior to infection. The mice were anesthetized by intraperitoneal injection of 1% pentobarbital (40 mg/kg, Sigma). The mice were then infected with K. pneumoniae 9170 to determine the minimum lethal dose for subsequent effective does and efficacy testing. Overnight cultures of K. pneumoniae 9170 were harvested and suspended in PBS. Subsequently, the cyclophosphamide-pretreated mice were intranasally injected with 25.0 µL of the bacterial suspension at designated doses (e.g., $1.0 \times 10^8$, $2.5 \times 10^8$, $5 \times 10^8$, $1.0 \times 10^9$, $2.0 \times 10^9$ CFU/mL, six mice per group). The minimum lethal dose (LD), the lowest concentration sufficient to cause 100% mortality, was determined from the survival rate of mice at 5 days post-infection by the BLISS method.

FIG. 9 provides a table 900 that presents the results of the following in vivo efficacy and toxicity tests respectively measured as a function of ED50/ED95 (the effective doses that cure 50% and 95% of infected mice, respectively), and LD50/LD5 (the lethal doses that kill 50% and 5% of the infected mice, respectively). The effective doses ED50 and ED95 doses of the respective polymers and imipenem for comparison, were tested using a bacteria-caused lung infection mouse model as follows. Firstly, a bacterial suspension with the minimum lethal dose (25.0 µL) was introduced to the above described cyclophosphamide-pretreated mice intranasally. The antimicrobial agents (e.g., the respective polymers and imipenem) were then respectively administered to different groups of mice (six mice per group) intraperitoneally, once daily for 3 days starting at 4.0 hours after infection at designated doses (e.g., 0.5, 1.0, 2.5, 5.0, 10.0 mg/kg for the polymers, and 1.0, 2.0, 5.0, 10.0, 20.0 mg/kg for imipenem, 0.2 mL/20 g, six mice per group). The number of surviving mice in each group was recorded for 5.0 day to estimate ED50 and ED95 via the BLISS method.

In vivo toxicity assessment used to determine the LD50 and LD5 of the same antimicrobial agents were tested as follows. The immunosuppressed mice were randomly divided into six groups (six mice per group). After dissolved in PBS, the polymers were administered intraperitoneally twice daily for 3.0 days at designated doses (e.g., 50, 60, 70, 80, 90 mg/kg for the polymer having Structures IV and V, and 140, 150, 160, 170,180 mg/kg for the polymer having Structure I, 0.2 mL/20 g, six mice per group). The number of surviving mice in each group was monitored for 7 days, and the values of LD50 (a dose at which half the mice are killed) and LD5 (a dose at which 5% of the mice are killed) were estimated by using the BLISS method. Afterwards, their toxicity towards major organs, such as liver, kidney, as well as the balance of electrolytes in the blood was evaluated.

As shown in FIG. 9, the three polymers having Structures I, IV and V showed outstanding in vivo efficacy against pneumoniae caused by MDR K. pneumoniae, with ED50 levels of 3.79 mg/kg for Structure IV, 2.97 mg/kg for Structure V, and 1.78 mg/kg for Structure I, all of which performed better than imipenem (with an ED50 of 5.93 mg/kg). The LD50 levels for the respective polymers also demonstrated substantially low toxicity. Of significant importance however is the huge jump in the therapeutic index (which is a combined function of a difference between the LD50 value and the ED50 value) of the subject antimicrobial guanidinium functionalized polymer having Structure I. In this regard, the therapeutic index jumps from 11.6 for Structure IV and 25.1 for Structure V to 88.8 for Structure I. This substantial (e.g., about 7× and 3× increase) in the therapeutic window of the subject guanidinium functionalized polymers indicates superior performance as potent antibacterial agent for MDR K pneumoniae infections and associated complications.

For further evaluating the in vivo anti-infective activities of the polymers, the number of bacteria in the blood, lung, liver, spleen and kidney of the tested mice were counted in according with the following protocol. Firstly, after anesthetized, the immunocompromised mice were instilled intranasally with $2.5 \times 10^7$ CFUs (three mice per group) of K. pneumoniae 9170. Then, mice were injected intraperitoneally with PBS, imipenem, and the respective polymers once daily for 3.0 days starting at 4.0 hours after infection at doses of ED50 (5.9 mg/kg for imipenem, 3.8 mg/kg for the polymer having Structure IV, 3.0 mg/kg for the polymer having Structure V, and 1.8 mg/kg for the polymer having Structure I. At 5.0 days post-infection, all mice were sacrificed to obtain blood and organs sample. Organs were removed and homogenized in 2.0 mL of PBS. The blood and homogenate samples were serially diluted and plated on MH agar plates and incubated overnight at 37° C. The number of bacterial colonies was then counted and the results were measures as mean 1 g (CFU/mL)±SD. The results are shown in FIG. 10

Figure 10:
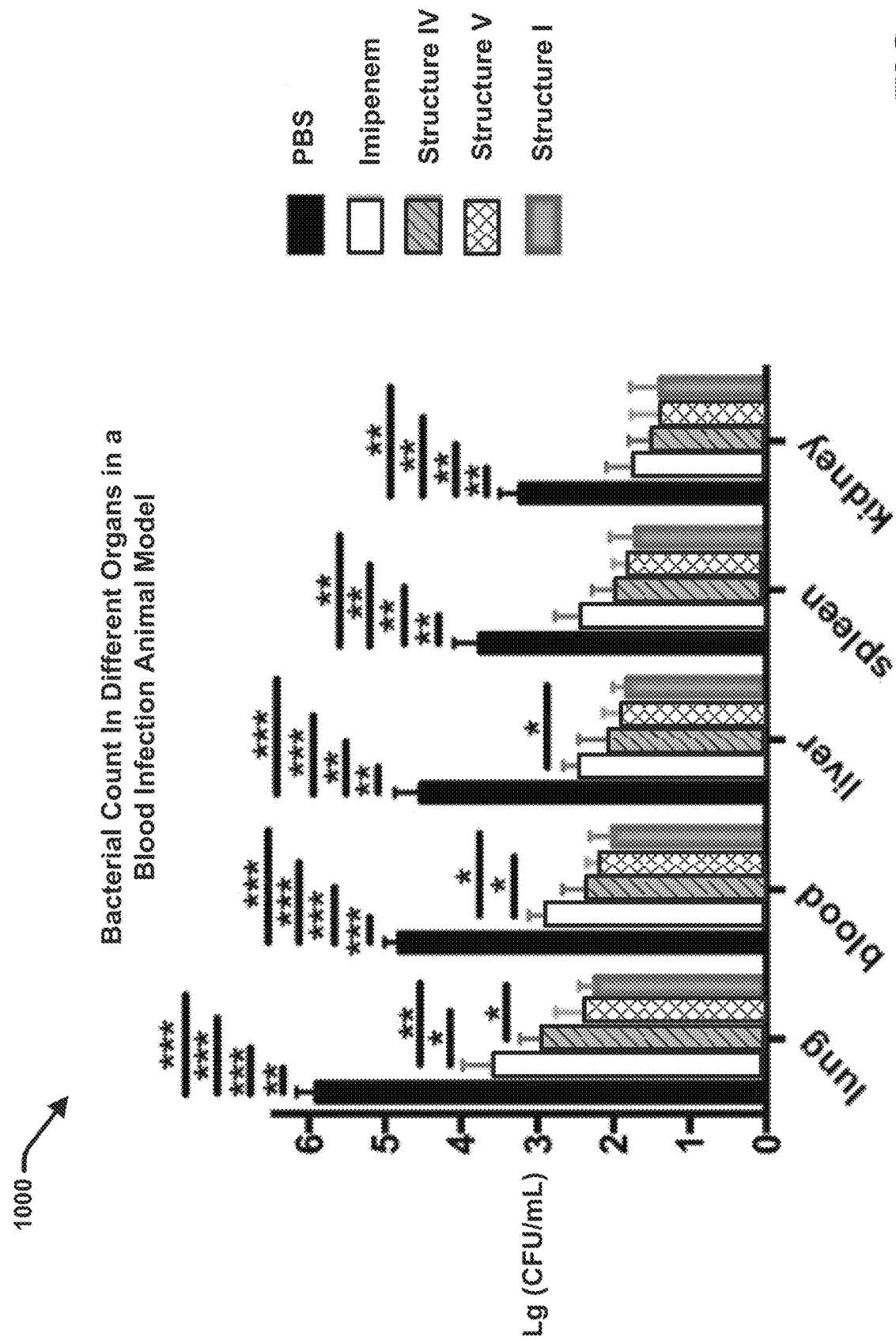
FIG. 10 illustrates another example, non-limiting graph that demonstrates the efficacy of bacterial removal from the lungs, blood, liver, spleen and kidneys, including the subject antimicrobial guanidinium macromolecules, against *K. pneumoniae* in the *K. pneumoniae*-caused lung infection mouse model, in accordance with one or more embodiments described herein.

In this regard, FIG. 10 presents a graph 1000 demonstrating the bacterial count of *K. pneumoniae* 9170 remaining in the lung, blood, liver, spleen and kidneys of the infected mice after 5.0 days post infection and treatment with the respective antimicrobials. The PBS and imipenem treatment were used as controls. In the embodiment shown, a significant reduction in the number of viable bacteria in each organ was observed after treatment with the respective polymers. However, the subject guanidinium functionalized polymers having Structure I still out-performed the other two polymers with the lowest concentration of bacteria remaining in all tested organs, demonstrating its potential in vivo antimicrobial activities.

Figure 11:
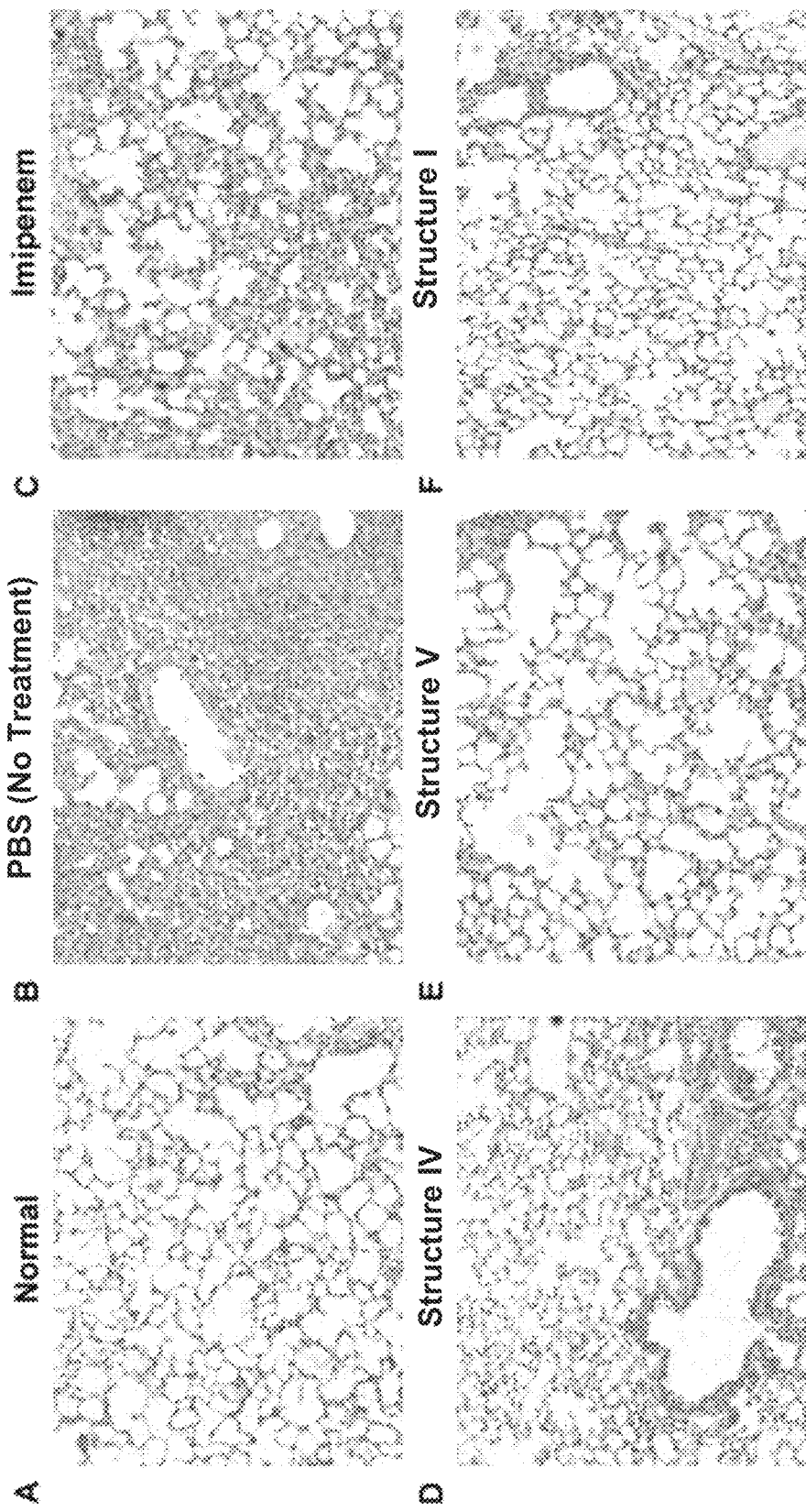
FIG. 11 presents morphological images of lung injury in infected mice with or without treatment by antimicrobial agents as assessed by haemotoxylin and eosin (H&E) staining histological analysis in accordance with one or more embodiments described herein.

Finally, to survey if the subject guanidinium functionalized polymers having Structure I could decrease infection-induced tissue injury, the morphological alterations in the lungs of infected mice were investigated by haemotoxylin and eosin (H&E) staining. The results are presented in FIG. 11. In this regard, FIG. 11 presents morphological images of lung injury in infected mice as assessed by H&E staining histological analysis. In accordance with the example histological analysis, the immunosuppressed mice were administered intra-nasally with *K. pneumoniae* 9170. At 4.0 hours post-infection, the mice received PBS (e.g., no treatment), imipenem, the polymer having Structure IV, the polymer having Structure V, and the polymer having Structure I, lung excised from normal mice was employed as the control. The results of the control are presented in image A, the results of the PBS are shown in image B, the results of imipenem treatment are shown in image C, the results of treatment with the polymer having Structure IV are shown in image D, the results of treatment with the polymer having Structure V are shown in image E, and the results of treatment with the polymer having Structure I are shown in image F. As shown in image B, the infected mice without treatment displayed inflammatory features, including inflammatory cells penetration, tissue damage and pulmonary carnification. Conversely, the lungs of mice treated with the polymers exhibited significantly reduced inflammation and tissue damage caused by the bacteria, wherein the treatment with the polymer having Structure I demonstrated the best performance. In this regard, comparison of image F and A reveals the treatment with the polymer having Structure I returned the lungs to substantially normal condition. Importantly, the treatments with the polymers did not cause damage to the healthy organs (heart, liver, kidney and spleen).

Figure 12:
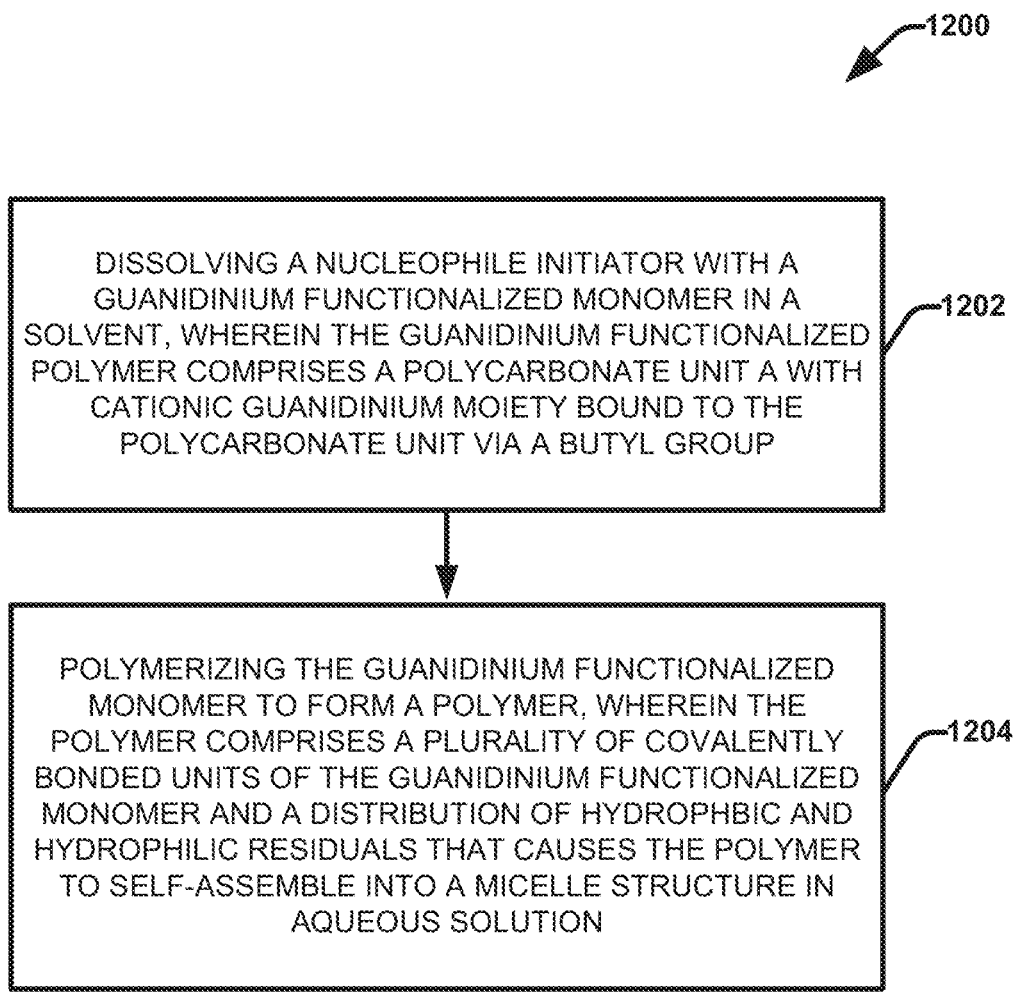
FIG. 12 illustrates a flow diagram of an example, non-limiting method that can facilitate generating one or more antimicrobial guanidinium polymers in accordance with one or more embodiments described herein.
Figure 13:
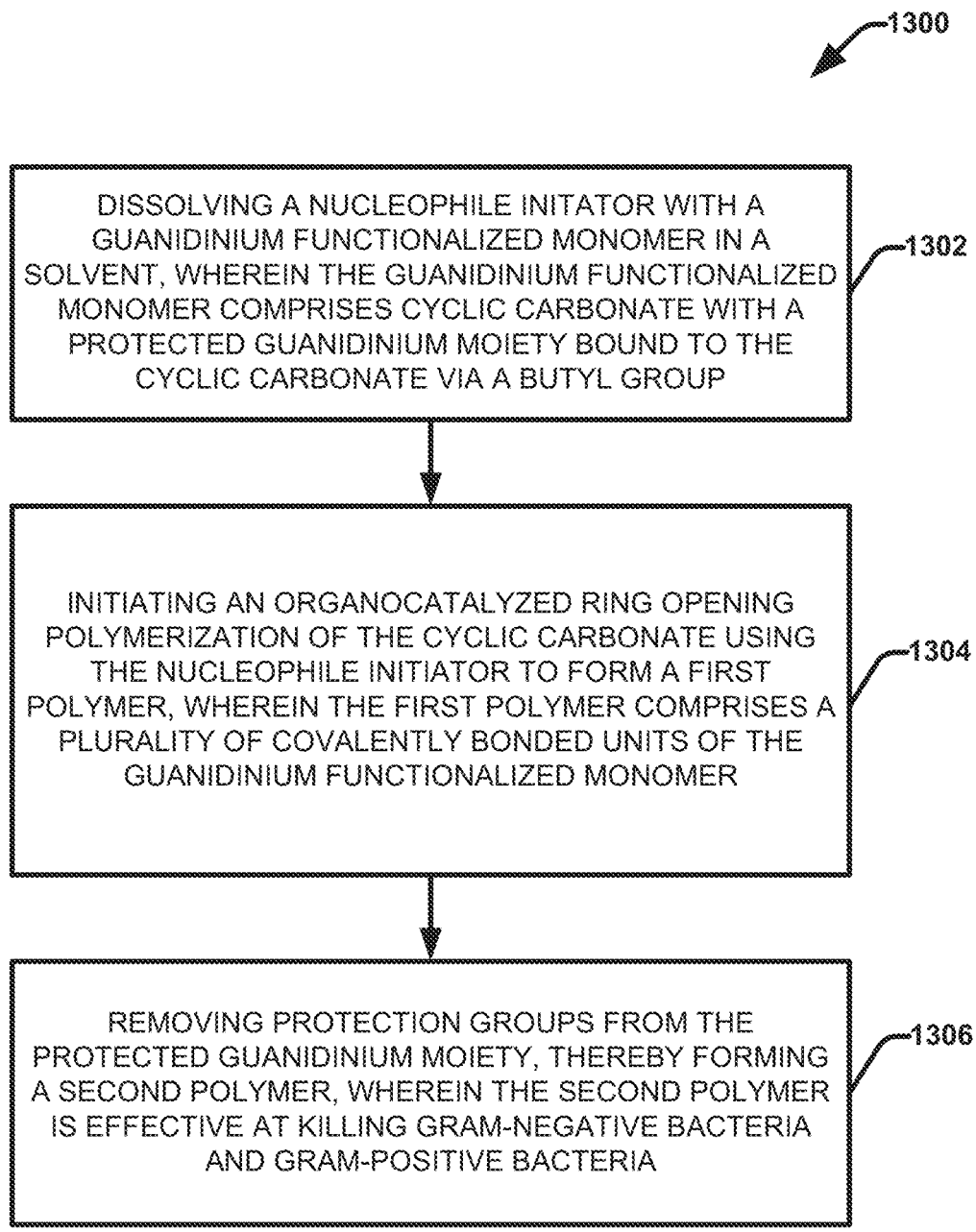
FIG. 13 illustrates a flow diagram of another example, non-limiting method that can facilitate generating one or more guanidinium polymers in accordance with one or more embodiments described herein.

FIGS. 12-13 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts can occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts can be required to implement a methodology in accordance with the disclosed subject matter. Repetitive description of like elements employed in respective embodiments is omitted for sake of brevity.

FIG. 12 illustrates a flow diagram of an example, non-limiting method 1200 that can facilitate generating one or more antimicrobial guanidinium polymers in accordance with one or more embodiments described herein. At 1202, a nucleophile initiator can be dissolved with a guanidinium functionalized monomer in a solvent, wherein the guanidinium functionalized monomer comprises a polycarbonate unit with a cationic guanidinium moiety bound to the polycarbonate unit via a butyl group. As a result, at 1204 the guanidinium functionalized monomer can be polymerized to form a polymer, wherein the polymer comprises a plurality of covalently bonded units of the guanidinium functionalized monomer, and distribution of hydrophobic and hydrophilic residuals that causes the polymer to self-assemble into a micelle structure in aqueous solution.

FIG. 13 illustrates a flow diagram of another example, non-limiting method 1300 that can facilitate generating one or more guanidinium polymers in accordance with one or more embodiments described herein. At 1302, a nucleophile initiator can be dissolved with a guanidinium functionalized monomer in a solvent, wherein the guanidinium functionalized monomer comprises cyclic carbonate with a protected guanidinium moiety bound to the cyclic carbonate via a butyl. At 1304, an organocatalyzed ring opening polymerization of the cyclic carbonate can be initiated using the nucleophile initiator to form a first polymer, wherein the first polymer comprises a plurality of covalently bonded units of the guanidinium functionalized monomer. At 1306, protection groups from the protected guanidinium moiety can be removed, thereby forming a second polymer, wherein the second polymer is effective at killing Gram-negative bacteria and Gram-positive bacteria.

FIG. 14 illustrates a high-level flow diagram of an example, non-limiting method that can facilitate killing of a pathogen with one or more guanidinium macromolecules in accordance with one or more embodiments described herein. At 1402, a bacteria microbe can be contacted with an antimicrobial polymer having a micelle structure in an aqueous solution, wherein the micelle structure locates hydrophobic residuals of the antimicrobial polymer inside the micelle structure and cationic guanidinium moieties exposed on an external surface of the micelle structure. At 1404, based on the contacting, charge naturalization of the bacterial membrane is facilitated via a counterion exchange between the cationic guanidinium moieties and negatively charged phosphate groups on the bacterial membrane. At 1406, translocation of the antimicrobial polymer through the bacterial membrane is further facilitated based on the charge neutralization.

The various structures and compositions described with reference to FIGS. 1-14 herein can regard chemical compounds that can be incorporated into a variety of applications. For example, said applications can include therapeutics, cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, agriculture including animals and plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption, and prevent as well as treat microbial infections in animals.

What has been described above includes mere examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. An antimicrobial guanidinium-functionalized polymer having a form of a micelle structure, the antimicrobial guanidinium-functionalized polymer, comprising:
   a hydrophobic molecular backbone structure with cationic guanidinium moieties respectively bound to the hydrophobic molecular backbone structure via butyl spacer groups, wherein hydrophobic residuals of the antimicrobial guanidinium-functionalized polymer are buried inside the micelle structure and the cationic guanidinium moieties are exposed on an external surface of the micelle structure to target pathogens.

2. The antimicrobial guanidinium-functionalized polyp of claim 1, wherein the hydrophobic molecular backbone comprises polycarbonate.

3. The antimicrobial guanidinium-functionalized polymer of claim 1, wherein the micelle structure has a size between 20 and 300 nanometers.

4. The antimicrobial guanidinium-functionalized polymer of claim 1, wherein the antimicrobial guanidinium-functionalized polymer self-assembles into the micelle structure in aqueous solution with a critical micelle concentration below 500 mg/L.

5. The antimicrobial guanidinium-functionalized polymer of claim 1, wherein the micelle structure mitigates exposure of the hydrophobic residuals to mammalian cells.

6. The antimicrobial guanidinium-functionalized polymer of claim 1, wherein the antimicrobial guanidinium-functionalized polymer is effective at killing Gram-negative bacteria and Gram-positive bacteria.

7. The antimicrobial guanidinium-functionalized polymer of claim 1, wherein the antimicrobial guanidinium-functionalized polymer is effective at killing multidrug resistant strains of *Klebsiella pneumonia*.

8. The antimicrobial guanidinium-functionalized polymer of claim 1, wherein the antimicrobial guanidinium-functionalized polymer is effective at killing bacteria selected from a group consisting of: *Acinetobacter baumannii, Escherichia coli, Staphylococcus aureus*, methicillin-resistant *Staphylococcus aureus, Pseudomonas aeruginosa* and *Enterococcus faccium*.

9. The antimicrobial guanidinium-functionalized polymer of claim 1, wherein the antimicrobial guanidinium-functionalized polymer has a chemical structure characterized by Structure I:

Structure I

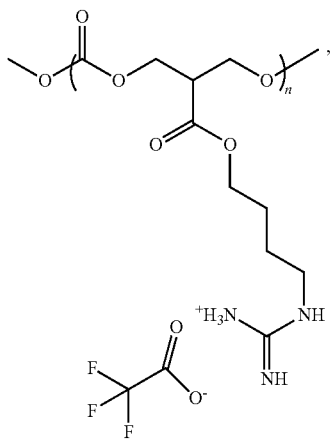

wherein n represents an integer between 5 and 65.

10. An antimicrobial polymer having a chemical structure characterized by Structure I:

Structure I

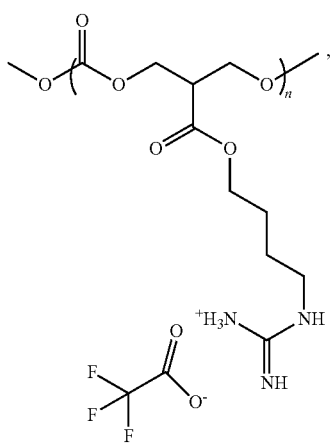

wherein n represents an integer between 10 and 30, and wherein the antimicrobial polymer has a form of a micelle with hydrophobic residuals of the antimicrobial polymer inside the micelle and hydrophilic residuals of the antimicrobial polymer on an external surface of the micelle.

11. The antimicrobial polymer of claim 10, wherein the antimicrobial polymer has a defined balance and distribution of the hydrophobic residuals relative to the hydrophilic residuals that causes the antimicrobial polymer to self-assemble into the nanostructure in the aqueous solution.

12. The antimicrobial polymer of claim 10, wherein the nanostructure is between 20 and 300 nanometers.

13. The antimicrobial polymer of claim 11, wherein the antimicrobial polymer is effective at killing Gram-negative bacteria and Gram-positive bacteria.

14. The antimicrobial polymer of claim 11, wherein the antimicrobial polymer is effective at treating lung infections caused by bacteria.

15. A method comprising:
contacting a bacteria microbe with an antimicrobial guanidinium-functionalized polymer having a form of a micelle structure in an aqueous solution, wherein the antimicrobial guanidinium-functionalized polymer comprises a hydrophobic molecular backbone structure with cationic guanidinium moieties respectively bound to the hydrophobic molecular backbone structure via butyl spacer groups, wherein hydrophobic residuals of the antimicrobial guanidium-functionalized polymer are buried inside the micelle structure and the cationic guanidinium moieties are exposed on an external surface of the micelle structure;
based on the contacting, facilitating charge naturalization of the bacterial membrane via a counterion exchange between the cationic guanidinium moieties and negatively charged phosphate groups on the bacterial membrane; and
facilitating translocation of the antimicrobial guanidinium-functionalized polymer through the bacterial membrane based on the charge neutralization.

16. The method of claim 15, wherein the facilitating the translocation through the bacterial membrane is based on disassembling of the micelle structure and exposure of the hydrophobic residuals to the bacteria microbe in response to the contacting.

17. The method of claim 15, wherein the hydrophobic molecular backbone structure is a polycarbonate.

18. The method of claim 15, wherein the bacteria microbe comprises a Gram-negative bacteria microbe or a Gram-positive bacteria microbe, and Wherein the antimicrobial guanidinium-functionalized polymer is effective against lung infections caused by the bacteria microbe.

19. The antimicrobial guanidinium-functionalized polymer claim 1, wherein the hydrophobic molecular backbone structure is a repeating structure that repeats a number of times ranging from greater than or equal to 5 and less than or equal to 65.

* * * * *